(12) United States Patent
Connor et al.

(10) Patent No.: US 9,358,140 B1
(45) Date of Patent: Jun. 7, 2016

(54) STENT WITH OUTER MEMBER TO EMBOLIZE AN ANEURYSM

(71) Applicants: Robert A. Connor, Forest Lake, MN (US); Tariq M. Janjua, Inver Grover Heights, MN (US); Mark Knudson, St. Paul, MN (US)

(72) Inventors: Robert A. Connor, Forest Lake, MN (US); Tariq M. Janjua, Inver Grover Heights, MN (US); Mark Knudson, St. Paul, MN (US)

(73) Assignee: Aneuclose LLC, Forest Lake, MN (US)

( * ) Notice: Subject to any disclaimer, the term of this patent is extended or adjusted under 35 U.S.C. 154(b) by 0 days.

(21) Appl. No.: 14/562,725

(22) Filed: Dec. 7, 2014

Related U.S. Application Data

(63) Continuation-in-part of application No. 12/592,116, filed on Nov. 18, 2009, now abandoned.

(51) Int. Cl.
| | |
|---|---|
| *A61F 2/82* | (2013.01) |
| *A61B 17/12* | (2006.01) |
| *A61B 17/00* | (2006.01) |
| *A61B 19/00* | (2006.01) |

(52) U.S. Cl.
CPC .............. *A61F 2/82* (2013.01); *A61B 17/1219* (2013.01); *A61B 17/12022* (2013.01); *A61B 17/12118* (2013.01); *A61B 2017/00898* (2013.01); *A61B 2019/5425* (2013.01); *A61F 2002/823* (2013.01)

(58) Field of Classification Search
CPC .............. A61F 2/07; A61F 2/82; A61F 2/89; A61F 2230/0069; A61F 2/915; A61F 2/90; A61F 2/86; A61F 2002/075; A61F 2002/823; A61F 2002/077; A61F 2210/0076; A61F 2220/0075; A61F 2002/067; A61F 2002/072; A61F 2/852; A61F 2/962
See application file for complete search history.

(56) References Cited

U.S. PATENT DOCUMENTS

| | | |
|---|---|---|
| 4,364,392 A | 12/1982 | Strother et al. |
| 4,994,069 A | 2/1991 | Ritchart et al. |
| 5,226,889 A | 7/1993 | Sheiban |
| 5,304,132 A | 4/1994 | Jang |
| 5,334,210 A | 8/1994 | Gianturco |
| 5,350,397 A | 9/1994 | Palermo et al. |
| 5,370,691 A | 12/1994 | Samson |
| 5,382,259 A | 1/1995 | Phelps et al. |

(Continued)

FOREIGN PATENT DOCUMENTS

WO PCT/US/2009/002537    4/2009

OTHER PUBLICATIONS

U.S. Appl. No. 12/387,637, filed 2009, Connor et al.

(Continued)

*Primary Examiner* — Christopher D Prone
*Assistant Examiner* — Ann Schillinger

(57) ABSTRACT

This invention is a stent to reduce blood flow to an aneurysm comprising: (a) an inner member, wherein this inner member is expanded from a first configuration to a second configuration within the parent vessel of an aneurysm, wherein the circumference of the second configuration is larger than the circumference of the first configuration; and (b) an outer member, wherein this outer member is less porous than the inner member, wherein this outer member covers or surrounds a first percentage of the surface area of the inner member when the inner structure is in the first configuration, wherein this outer member covers or surrounds a second percentage of the surface area of the inner member when the inner structure is in the second configuration, and wherein the second percentage less than the first percentage.

1 Claim, 9 Drawing Sheets

(56) References Cited

U.S. PATENT DOCUMENTS

| | | | |
|---|---|---|---|
| 5,405,379 | A | 4/1995 | Lane |
| 5,411,549 | A | 5/1995 | Peters |
| 5,423,829 | A | 6/1995 | Pham et al. |
| 5,443,478 | A | 8/1995 | Purdy |
| 5,522,822 | A | 6/1996 | Phelps et al. |
| 5,536,252 | A | 7/1996 | Imran et al. |
| 5,582,619 | A | 12/1996 | Ken |
| 5,603,722 | A | 2/1997 | Phan et al. |
| 5,624,449 | A | 4/1997 | Pham et al. |
| 5,624,461 | A | 4/1997 | Mariant |
| 5,624,685 | A | 4/1997 | Takahashi et al. |
| 5,639,277 | A | 6/1997 | Mariant et al. |
| 5,645,559 | A | 7/1997 | Hachtman et al. |
| 5,649,949 | A | 7/1997 | Wallace et al. |
| 5,690,666 | A | 11/1997 | Berenstein et al. |
| 5,690,667 | A | 11/1997 | Gia |
| 5,693,088 | A | 12/1997 | Lazarus |
| 5,702,361 | A | 12/1997 | Evans et al. |
| 5,718,711 | A | 2/1998 | Berenstein et al. |
| 5,723,004 | A | 3/1998 | Dereume et al. |
| 5,733,294 | A | 3/1998 | Forber et al. |
| 5,733,329 | A | 3/1998 | Wallace et al. |
| 5,743,905 | A | 4/1998 | Eder et al. |
| 5,749,891 | A | 5/1998 | Ken et al. |
| 5,749,894 | A | 5/1998 | Engelson |
| 5,766,160 | A | 6/1998 | Samson et al. |
| 5,766,219 | A | 6/1998 | Horton |
| 5,769,882 | A | 6/1998 | Fogarty et al. |
| 5,769,884 | A | 6/1998 | Solovay |
| 5,776,097 | A | 7/1998 | Massoud |
| 5,785,679 | A | 7/1998 | Abolfathi et al. |
| 5,795,331 | A | 8/1998 | Cragg et al. |
| 5,800,453 | A | 9/1998 | Gia |
| 5,800,455 | A | 9/1998 | Palermo et al. |
| 5,826,587 | A | 10/1998 | Berenstein et al. |
| 5,833,657 | A | 11/1998 | Reinhardt et al. |
| 5,833,705 | A | 11/1998 | Ken et al. |
| 5,836,966 | A | 11/1998 | St. Germain |
| 5,853,418 | A | 12/1998 | Ken et al. |
| 5,868,780 | A | 2/1999 | Lashinski et al. |
| 5,873,907 | A | 2/1999 | Frantzen |
| 5,888,546 | A | 3/1999 | Ji et al. |
| 5,891,130 | A | 4/1999 | Palermo et al. |
| 5,894,022 | A | 4/1999 | Ji et al. |
| 5,911,731 | A | 6/1999 | Pham et al. |
| 5,916,235 | A | 6/1999 | Guglielmi |
| 5,922,019 | A | 7/1999 | Hankh et al. |
| 5,925,059 | A | 7/1999 | Palermo et al. |
| 5,928,260 | A | 7/1999 | Chin et al. |
| 5,935,145 | A | 8/1999 | Villar et al. |
| 5,935,148 | A | 8/1999 | Villar et al. |
| 5,938,697 | A | 8/1999 | Killion et al. |
| 5,941,249 | A | 8/1999 | Maynard |
| 5,941,888 | A | 8/1999 | Wallace et al. |
| 5,948,018 | A | 9/1999 | Dereume et al. |
| 5,951,599 | A | 9/1999 | McCrory |
| 5,957,948 | A | 9/1999 | Mariant |
| 5,957,975 | A | 9/1999 | Lafont et al. |
| 5,964,797 | A | 10/1999 | Ho |
| 5,980,514 | A | 11/1999 | Kupiecki et al. |
| 6,004,338 | A | 12/1999 | Ken et al. |
| 6,007,573 | A | 12/1999 | Wallace et al. |
| 6,013,084 | A | 1/2000 | Ken et al. |
| 6,015,424 | A | 1/2000 | Rosenbluth et al. |
| 6,015,433 | A | 1/2000 | Roth |
| 6,017,977 | A | 1/2000 | Evans et al. |
| 6,024,754 | A | 2/2000 | Engelson |
| 6,024,765 | A | 2/2000 | Wallace et al. |
| 6,027,526 | A | 2/2000 | Limon et al. |
| 6,033,423 | A | 3/2000 | Ken et al. |
| 6,036,720 | A | 3/2000 | Abrams et al. |
| 6,063,070 | A | 5/2000 | Eder |
| 6,063,104 | A | 5/2000 | Villar et al. |
| 6,063,111 | A | 5/2000 | Hieshima et al. |
| 6,071,298 | A | 6/2000 | Lashinski et al. |
| 6,074,407 | A | 6/2000 | Levine et al. |
| 6,086,610 | A | 7/2000 | Duerig et al. |
| 6,093,199 | A | 7/2000 | Brown et al. |
| 6,096,021 | A | 8/2000 | Helm et al. |
| 6,096,034 | A | 8/2000 | Kupiecki et al. |
| 6,096,175 | A | 8/2000 | Roth |
| 6,099,546 | A | 8/2000 | Gia |
| 6,099,559 | A | 8/2000 | Nolting |
| 6,123,712 | A | 9/2000 | Di Caprio et al. |
| 6,123,714 | A | 9/2000 | Gia et al. |
| 6,136,011 | A | 10/2000 | Stambaugh |
| 6,139,564 | A | 10/2000 | Teoh |
| 6,140,452 | A | 10/2000 | Felt et al. |
| 6,143,007 | A | 11/2000 | Mariant et al. |
| 6,149,681 | A | 11/2000 | Houser et al. |
| 6,159,165 | A | 12/2000 | Ferrera et al. |
| 6,159,238 | A | 12/2000 | Killion et al. |
| 6,165,193 | A | 12/2000 | Greene et al. |
| 6,165,212 | A | 12/2000 | Dereume et al. |
| 6,168,592 | B1 | 1/2001 | Kupiecki et al. |
| 6,168,615 | B1 | 1/2001 | Ken et al. |
| 6,168,622 | B1 | 1/2001 | Mazzocchi |
| 6,187,027 | B1 | 2/2001 | Mariant et al. |
| 6,190,406 | B1 | 2/2001 | Duerig et al. |
| 6,193,728 | B1 | 2/2001 | Ken et al. |
| 6,210,429 | B1 | 4/2001 | Vardi et al. |
| 6,221,066 | B1 | 4/2001 | Ferrera et al. |
| 6,231,586 | B1 | 5/2001 | Mariant |
| 6,231,597 | B1 | 5/2001 | Deem et al. |
| 6,238,403 | B1 | 5/2001 | Greene et al. |
| 6,254,592 | B1 | 7/2001 | Samson et al. |
| 6,258,115 | B1 | 7/2001 | Dubrul |
| 6,258,117 | B1 | 7/2001 | Camrud et al. |
| 6,270,523 | B1 | 8/2001 | Herweck et al. |
| 6,273,910 | B1 | 8/2001 | Limon |
| 6,273,911 | B1 | 8/2001 | Cox et al. |
| 6,280,457 | B1 | 8/2001 | Wallace et al. |
| 6,281,263 | B1 | 8/2001 | Evans et al. |
| 6,287,318 | B1 | 9/2001 | Villar et al. |
| 6,299,619 | B1 | 10/2001 | Greene et al. |
| 6,306,177 | B1 | 10/2001 | Felt et al. |
| 6,309,367 | B1 | 10/2001 | Boock |
| 6,309,413 | B1 | 10/2001 | Dereume et al. |
| 6,312,421 | B1 | 11/2001 | Boock |
| 6,312,463 | B1 | 11/2001 | Rourke et al. |
| 6,331,191 | B1 | 12/2001 | Chobotov |
| 6,335,384 | B1 | 1/2002 | Evans et al. |
| 6,342,068 | B1 | 1/2002 | Thompson |
| 6,344,041 | B1 | 2/2002 | Kupiecki et al. |
| 6,344,048 | B1 | 2/2002 | Chin et al. |
| 6,346,117 | B1 | 2/2002 | Greenhalgh |
| 6,350,270 | B1 | 2/2002 | Roue |
| 6,371,972 | B1 | 4/2002 | Wallace et al. |
| 6,375,668 | B1 | 4/2002 | Gifford et al. |
| 6,375,669 | B1 | 4/2002 | Rosenbluth et al. |
| 6,379,373 | B1 | 4/2002 | Sawhney et al. |
| 6,383,174 | B1 | 5/2002 | Eder |
| 6,391,037 | B1 | 5/2002 | Greenhalgh |
| 6,395,018 | B1 | 5/2002 | Castaneda |
| 6,398,803 | B1 | 6/2002 | Layne et al. |
| 6,406,490 | B1 | 6/2002 | Roth |
| 6,409,721 | B1 | 6/2002 | Wheelock et al. |
| 6,409,749 | B1 | 6/2002 | Maynard |
| 6,416,543 | B1 | 7/2002 | Hilaire et al. |
| 6,419,685 | B2 | 7/2002 | Di Caprio et al. |
| 6,423,085 | B1 | 7/2002 | Murayama et al. |
| 6,428,558 | B1 | 8/2002 | Jones et al. |
| 6,432,128 | B1 | 8/2002 | Wallace et al. |
| 6,454,738 | B1 | 9/2002 | Tran et al. |
| 6,454,780 | B1 | 9/2002 | Wallace |
| 6,458,119 | B1 | 10/2002 | Berenstein et al. |
| 6,463,317 | B1 | 10/2002 | Kucharczyk et al. |
| 6,468,302 | B2 | 10/2002 | Cox et al. |
| 6,471,672 | B1 | 10/2002 | Brown et al. |
| 6,475,233 | B2 | 11/2002 | Trozera |
| 6,475,236 | B1 | 11/2002 | Roubin et al. |
| 6,485,509 | B2 | 11/2002 | Killion et al. |
| 6,485,510 | B1 | 11/2002 | Camrud et al. |
| 6,497,722 | B1 | 12/2002 | Von Oepen et al. |

(56) References Cited

U.S. PATENT DOCUMENTS

| | | |
|---|---|---|
| 6,500,190 B2 | 12/2002 | Greene et al. |
| 6,506,201 B2 | 1/2003 | Di Caprio et al. |
| 6,506,204 B2 | 1/2003 | Mazzocchi |
| 6,511,468 B1 | 1/2003 | Cragg et al. |
| 6,511,505 B2 | 1/2003 | Cox et al. |
| 6,520,985 B1 | 2/2003 | Burpee et al. |
| 6,520,987 B1 | 2/2003 | Plante |
| 6,527,919 B1 | 3/2003 | Roth |
| 6,533,801 B2 | 3/2003 | Wallace et al. |
| 6,547,804 B2 | 4/2003 | Porter et al. |
| 6,551,305 B2 | 4/2003 | Ferrera et al. |
| 6,558,414 B2 | 5/2003 | Layne |
| 6,569,190 B2 | 5/2003 | Whalen et al. |
| 6,569,193 B1 | 5/2003 | Cox et al. |
| 6,579,305 B1 | 6/2003 | Lashinski |
| 6,579,314 B1 | 6/2003 | Lombardi et al. |
| 6,585,748 B1 | 7/2003 | Jeffree |
| 6,585,753 B2 | 7/2003 | Eder et al. |
| 6,585,758 B1 | 7/2003 | Chouinard et al. |
| 6,589,230 B2 | 7/2003 | Gia et al. |
| 6,599,316 B2 | 7/2003 | Vardi et al. |
| 6,602,261 B2 | 8/2003 | Greene et al. |
| 6,602,269 B2 | 8/2003 | Wallace et al. |
| 6,602,284 B2 | 8/2003 | Cox et al. |
| 6,603,994 B2 | 8/2003 | Wallace et al. |
| 6,605,056 B2 | 8/2003 | Eidenschink et al. |
| 6,605,101 B1 | 8/2003 | Schaefer et al. |
| 6,605,111 B2 | 8/2003 | Bose et al. |
| 6,613,074 B1 | 9/2003 | Mitelberg et al. |
| 6,616,617 B1 | 9/2003 | Ferrera et al. |
| 6,623,493 B2 | 9/2003 | Wallace et al. |
| 6,629,947 B1 | 10/2003 | Sahatjian et al. |
| 6,645,237 B2 | 11/2003 | Klumb et al. |
| 6,652,576 B1 | 11/2003 | Stalker |
| 6,656,214 B1 | 12/2003 | Fogarty et al. |
| 6,660,020 B2 | 12/2003 | Wallace et al. |
| 6,660,032 B2 | 12/2003 | Klumb et al. |
| 6,669,719 B2 | 12/2003 | Wallace et al. |
| 6,669,723 B2 | 12/2003 | Killion et al. |
| 6,673,103 B1 | 1/2004 | Golds et al. |
| 6,676,701 B2 | 1/2004 | Rourke et al. |
| 6,689,148 B2 | 2/2004 | Sawhney et al. |
| 6,699,277 B1 | 3/2004 | Freidberg et al. |
| 6,719,783 B2 | 4/2004 | Lentz et al. |
| 6,723,108 B1 | 4/2004 | Jones et al. |
| 6,746,468 B1 | 6/2004 | Sepetka et al. |
| 6,746,475 B1 | 6/2004 | Rivelli |
| 6,770,087 B2 | 8/2004 | Layne et al. |
| 6,780,196 B2 | 8/2004 | Chin et al. |
| 6,786,920 B2 | 9/2004 | Shannon et al. |
| 6,790,225 B1 | 9/2004 | Shannon et al. |
| 6,796,997 B1 | 9/2004 | Penn et al. |
| 6,802,851 B2 | 10/2004 | Jones et al. |
| 6,811,560 B2 | 11/2004 | Jones et al. |
| 6,814,754 B2 | 11/2004 | Greenhalgh |
| 6,818,018 B1 | 11/2004 | Sawhney |
| 6,833,003 B2 | 12/2004 | Jones et al. |
| 6,835,203 B1 | 12/2004 | Vardi et al. |
| 6,855,153 B2 | 2/2005 | Saadat |
| 6,855,154 B2 | 2/2005 | Abdel-Gawwad |
| 6,860,899 B1 | 3/2005 | Rivelli |
| 6,899,730 B1 | 5/2005 | Rivelli |
| 6,913,618 B2 | 7/2005 | Denardo et al. |
| 6,916,337 B2 | 7/2005 | Roth |
| 6,929,658 B1 | 8/2005 | Freidberg et al. |
| 6,958,061 B2 | 10/2005 | Truckai et al. |
| 6,962,602 B2 | 11/2005 | Vardi et al. |
| 6,964,657 B2 | 11/2005 | Cragg et al. |
| 6,969,401 B1 | 11/2005 | Marotta et al. |
| 6,979,344 B2 | 12/2005 | Jones et al. |
| 6,984,240 B1 | 1/2006 | Ken et al. |
| 6,994,721 B2 | 2/2006 | Israel |
| 7,001,422 B2 | 2/2006 | Escamilla et al. |
| 7,014,645 B2 | 3/2006 | Greene et al. |
| 7,029,486 B2 | 4/2006 | Schaefer et al. |
| 7,029,487 B2 | 4/2006 | Greene et al. |
| 7,033,374 B2 | 4/2006 | Schaefer et al. |
| 7,033,385 B2 | 4/2006 | Eder et al. |
| 7,037,327 B2 | 5/2006 | Salmon et al. |
| 7,037,330 B1 | 5/2006 | Rivelli et al. |
| 7,041,129 B2 | 5/2006 | Rourke et al. |
| 7,052,510 B1 | 5/2006 | Richter |
| 7,052,513 B2 | 5/2006 | Thompson |
| 7,060,091 B2 | 6/2006 | Killion et al. |
| 7,070,609 B2 | 7/2006 | West |
| 7,081,129 B2 | 7/2006 | Chobotov |
| 7,083,632 B2 | 8/2006 | Avellanet et al. |
| 7,083,640 B2 | 8/2006 | Lombardi et al. |
| 7,083,643 B2 | 8/2006 | Whalen et al. |
| 7,112,216 B2 | 9/2006 | Gregorich |
| 7,118,656 B2 | 10/2006 | Roth |
| 7,128,736 B1 | 10/2006 | Abrams et al. |
| 7,137,993 B2 | 11/2006 | Acosta et al. |
| 7,141,063 B2 | 11/2006 | White et al. |
| 7,147,655 B2 | 12/2006 | Chermoni |
| 7,147,659 B2 | 12/2006 | Jones |
| 7,147,660 B2 | 12/2006 | Chobotov et al. |
| 7,147,661 B2 | 12/2006 | Chobotov et al. |
| 7,153,323 B1 | 12/2006 | Teoh et al. |
| 7,156,871 B2 | 1/2007 | Jones et al. |
| 7,182,744 B2 | 2/2007 | Yamasaki et al. |
| 7,186,263 B2 | 3/2007 | Golds et al. |
| 7,195,636 B2 | 3/2007 | Avellanet et al. |
| 7,195,648 B2 | 3/2007 | Jones et al. |
| 7,201,762 B2 | 4/2007 | Greene et al. |
| 7,211,109 B2 | 5/2007 | Thompson |
| 7,220,270 B2 | 5/2007 | Sawhney et al. |
| 7,226,475 B2 | 6/2007 | Lenz et al. |
| 7,229,461 B2 | 6/2007 | Chin et al. |
| 7,231,260 B2 | 6/2007 | Wallace et al. |
| 7,232,461 B2 | 6/2007 | Ramer |
| 7,235,098 B2 | 6/2007 | Palmaz |
| 7,238,194 B2 | 7/2007 | Monstadt et al. |
| 7,241,301 B2 | 7/2007 | Thramann et al. |
| 7,241,308 B2 | 7/2007 | Andreas et al. |
| 7,244,261 B2 | 7/2007 | Lorenzo et al. |
| 7,247,159 B2 | 7/2007 | Lorenzo et al. |
| 7,288,112 B2 | 10/2007 | Denardo et al. |
| 7,294,123 B2 | 11/2007 | Jones et al. |
| 7,294,137 B2 | 11/2007 | Rivelli et al. |
| 7,294,146 B2 | 11/2007 | Chew et al. |
| 7,300,459 B2 | 11/2007 | Heuser |
| 7,300,661 B2 | 11/2007 | Henson et al. |
| 7,306,598 B2 | 12/2007 | Truckai et al. |
| 7,306,622 B2 | 12/2007 | Jones et al. |
| 7,306,624 B2 | 12/2007 | Yodfat et al. |
| 7,309,351 B2 | 12/2007 | Escamilla et al. |
| 7,309,352 B2 | 12/2007 | Eder et al. |
| 7,311,861 B2 | 12/2007 | Lanphere et al. |
| 7,323,005 B2 | 1/2008 | Wallace et al. |
| 7,326,225 B2 | 2/2008 | Ferrera et al. |
| 7,326,236 B2 | 2/2008 | Andreas et al. |
| 7,331,974 B2 | 2/2008 | Schaefer et al. |
| 7,338,511 B2 | 3/2008 | Mirigian et al. |
| 7,361,367 B2 | 4/2008 | Henson et al. |
| 7,374,568 B2 | 5/2008 | Whalen et al. |
| 7,384,426 B2 | 6/2008 | Wallace et al. |
| 7,402,169 B2 | 7/2008 | Killion et al. |
| 7,410,482 B2 | 8/2008 | Murphy et al. |
| 7,413,573 B2 | 8/2008 | Hartley et al. |
| 7,414,038 B2 | 8/2008 | Kinugasa et al. |
| 7,442,382 B2 | 10/2008 | Henson et al. |
| 7,449,236 B2 | 11/2008 | Lanphere et al. |
| 7,455,753 B2 | 11/2008 | Roth |
| 7,481,821 B2 | 1/2009 | Fogarty et al. |
| 7,483,558 B2 | 1/2009 | Greene et al. |
| 7,485,123 B2 | 2/2009 | Porter |
| 7,491,214 B2 | 2/2009 | Greene et al. |
| 7,491,226 B2 | 2/2009 | Palmaz et al. |
| 7,491,229 B2 | 2/2009 | Eder et al. |
| 7,520,893 B2 | 4/2009 | Rivelli |
| 7,537,609 B2 | 5/2009 | Davidson et al. |
| 7,547,321 B2 | 6/2009 | Silvestri et al. |
| 7,563,270 B2 | 7/2009 | Gumm |

(56) References Cited

U.S. PATENT DOCUMENTS

| | | |
|---|---|---|
| 7,569,066 B2 | 8/2009 | Gerberding et al. |
| 7,572,288 B2 | 8/2009 | Cox |
| 7,572,290 B2 | 8/2009 | Yodfat et al. |
| 7,588,597 B2 | 9/2009 | Frid |
| 7,588,780 B2 | 9/2009 | Buiser et al. |
| 7,588,825 B2 | 9/2009 | Bell et al. |
| 7,608,088 B2 | 10/2009 | Jones et al. |
| 7,611,530 B2 | 11/2009 | Pomeranz et al. |
| 7,615,071 B2 | 11/2009 | Chobotov |
| 7,621,928 B2 | 11/2009 | Thramann et al. |
| 7,641,680 B2 | 1/2010 | Palmaz et al. |
| 7,645,298 B2 | 1/2010 | Hartley et al. |
| 7,651,525 B2 | 1/2010 | Dolan |
| 7,666,220 B2 | 2/2010 | Evans et al. |
| 7,666,333 B2 | 2/2010 | Lanphere et al. |
| 7,691,124 B2 | 4/2010 | Balgobin |
| 7,695,484 B2 | 4/2010 | Wallace et al. |
| 7,695,488 B2 | 4/2010 | Berenstein et al. |
| 7,695,507 B2 | 4/2010 | Rivelli et al. |
| 7,695,509 B2 | 4/2010 | Rourke et al. |
| 7,704,274 B2 | 4/2010 | Boyle et al. |
| 7,708,754 B2 | 5/2010 | Balgobin et al. |
| 7,708,755 B2 | 5/2010 | Davis et al. |
| 7,713,264 B2 | 5/2010 | Murphy et al. |
| 7,736,671 B2 | 6/2010 | DiCarlo et al. |
| 7,744,610 B2 | 6/2010 | Hausen |
| 7,744,652 B2 | 6/2010 | Morsi |
| 7,749,242 B2 | 7/2010 | Tran et al. |
| 7,758,892 B1 | 7/2010 | Chen et al. |
| 7,763,011 B2 | 7/2010 | Ortiz et al. |
| 7,766,933 B2 | 8/2010 | Davis et al. |
| 7,766,955 B2 | 8/2010 | Vardi et al. |
| 7,769,603 B2 | 8/2010 | Jung et al. |
| 7,776,079 B2 | 8/2010 | Gumm |
| 7,780,645 B2 | 8/2010 | Jones |
| 7,780,719 B2 | 8/2010 | Killion et al. |
| 7,799,047 B2 | 9/2010 | Greene et al. |
| 7,799,052 B2 | 9/2010 | Balgobin et al. |
| 7,803,179 B2 | 9/2010 | Denison |
| 7,803,180 B2 | 9/2010 | Burpee et al. |
| 7,811,300 B2 | 10/2010 | Feller et al. |
| 7,811,305 B2 | 10/2010 | Balgobin et al. |
| 7,818,084 B2 | 10/2010 | Boyden et al. |
| 7,819,891 B2 | 10/2010 | Balgobin et al. |
| 7,819,892 B2 | 10/2010 | Balgobin et al. |
| 7,842,054 B2 | 11/2010 | Greene et al. |
| 7,842,377 B2 | 11/2010 | Lanphere et al. |
| 7,850,725 B2 | 12/2010 | Vardi et al. |
| 7,857,843 B2 | 12/2010 | Henderson |
| 7,862,608 B2 | 1/2011 | Hogendijk et al. |
| 7,875,044 B2 | 1/2011 | Feller et al. |
| 7,883,526 B2 | 2/2011 | Jones et al. |
| 7,892,273 B2 | 2/2011 | George et al. |
| 7,892,279 B2 | 2/2011 | Davidson et al. |
| 7,896,899 B2 | 3/2011 | Patterson et al. |
| 7,901,445 B2 | 3/2011 | Wallace et al. |
| 7,905,913 B2 | 3/2011 | Chew et al. |
| 7,914,574 B2 | 3/2011 | Schmid et al. |
| 7,914,639 B2 | 3/2011 | Layne et al. |
| 7,918,881 B2 | 4/2011 | Andreas et al. |
| 7,922,755 B2 | 4/2011 | Acosta et al. |
| 7,935,142 B2 | 5/2011 | Gregorich |
| 7,938,845 B2 | 5/2011 | Aganon et al. |
| 7,942,925 B2 | 5/2011 | Yodfat et al. |
| 7,947,071 B2 | 5/2011 | Schmid et al. |
| 7,955,382 B2 | 6/2011 | Flanagan et al. |
| 7,959,662 B2 | 6/2011 | Erbel et al. |
| 7,963,987 B2 | 6/2011 | Melsheimer et al. |
| 7,976,527 B2 | 7/2011 | Cragg et al. |
| 7,976,823 B2 | 7/2011 | Lanphere et al. |
| 7,985,238 B2 | 7/2011 | Balgobin et al. |
| 7,988,721 B2 | 8/2011 | Morris et al. |
| 7,993,364 B2 | 8/2011 | Morsi |
| 8,002,789 B2 | 8/2011 | Ramzipoor et al. |
| 8,003,180 B2 | 8/2011 | Goffena et al. |
| 8,007,529 B2 | 8/2011 | Yan |
| 8,012,192 B2 | 9/2011 | Eidenschink et al. |
| 8,012,197 B2 | 9/2011 | Bashiri et al. |
| 8,016,853 B2 | 9/2011 | Griffen et al. |
| 8,016,870 B2 | 9/2011 | Chew et al. |
| 8,016,871 B2 | 9/2011 | Chew et al. |
| 8,016,876 B2 | 9/2011 | Gregorich et al. |
| 8,016,878 B2 | 9/2011 | Meyer et al. |
| 8,019,413 B2 | 9/2011 | Ferren et al. |
| 8,021,416 B2 | 9/2011 | Abrams |
| 8,024,036 B2 | 9/2011 | Ferren et al. |
| 8,034,073 B2 | 10/2011 | Davis et al. |
| 8,038,706 B2 | 10/2011 | Eidenschink et al. |
| 8,038,708 B2 | 10/2011 | Case et al. |
| 8,048,140 B2 | 11/2011 | Purdy |
| 8,052,736 B2 | 11/2011 | Doig et al. |
| 8,057,495 B2 | 11/2011 | Pal et al. |
| 8,062,379 B2 | 11/2011 | Morsi |
| 8,066,036 B2 | 11/2011 | Monetti et al. |
| 8,067,071 B2 | 11/2011 | Farnsworth et al. |
| 8,070,792 B2 | 12/2011 | Gregorich et al. |
| 8,075,585 B2 | 12/2011 | Lee et al. |
| 8,095,382 B2 | 1/2012 | Boyden et al. |
| 8,100,960 B2 | 1/2012 | Bruszewski |
| 8,133,256 B2 | 3/2012 | Wilson et al. |
| 8,142,456 B2 | 3/2012 | Rosqueta et al. |
| 8,147,534 B2 | 4/2012 | Berez et al. |
| 8,147,537 B2 | 4/2012 | Boyden et al. |
| 8,163,003 B2 | 4/2012 | Boyden et al. |
| 8,172,862 B2 | 5/2012 | Wallace et al. |
| 8,172,895 B2 | 5/2012 | Anderson et al. |
| 8,187,315 B1 | 5/2012 | Clauson et al. |
| 8,202,292 B2 | 6/2012 | Kellett |
| 8,211,141 B2 | 7/2012 | Davis et al. |
| 8,211,160 B2 | 7/2012 | Garrison et al. |
| 8,221,447 B2 | 7/2012 | Solar et al. |
| 8,226,660 B2 | 7/2012 | Teoh et al. |
| 8,226,706 B2 | 7/2012 | Hartley et al. |
| 8,236,042 B2 | 8/2012 | Berez et al. |
| 8,246,672 B2 | 8/2012 | Osborne |
| 8,252,040 B2 | 8/2012 | Cox |
| 8,257,421 B2 | 9/2012 | Berez et al. |
| 8,257,431 B2 | 9/2012 | Henderson et al. |
| 8,257,684 B2 | 9/2012 | Covalin et al. |
| 8,262,607 B2 | 9/2012 | Porter |
| 8,262,686 B2 | 9/2012 | Fogarty et al. |
| 8,267,923 B2 | 9/2012 | Murphy et al. |
| 8,267,955 B2 | 9/2012 | Patterson et al. |
| 8,267,985 B2 | 9/2012 | Garcia et al. |
| 8,267,986 B2 | 9/2012 | Berez et al. |
| 8,273,100 B2 | 9/2012 | Martinez |
| 8,273,101 B2 | 9/2012 | Garcia et al. |
| 8,277,500 B2 | 10/2012 | Schmid et al. |
| 8,282,679 B2 | 10/2012 | Denison |
| 8,292,914 B2 | 10/2012 | Morsi |
| 8,292,944 B2 | 10/2012 | Schmid et al. |
| 8,308,751 B2 | 11/2012 | Gerberding |
| 8,313,504 B2 | 11/2012 | Do et al. |
| 8,323,306 B2 | 12/2012 | Schaefer et al. |
| 8,328,860 B2 | 12/2012 | Strauss et al. |
| 8,353,943 B2 | 1/2013 | Kuppurathanam et al. |
| 8,357,178 B2 | 1/2013 | Grandfield et al. |
| 8,357,179 B2 | 1/2013 | Grandfield et al. |
| 8,357,180 B2 | 1/2013 | Feller et al. |
| 8,361,104 B2 | 1/2013 | Jones et al. |
| 8,361,106 B2 | 1/2013 | Solar et al. |
| 8,372,062 B2 | 2/2013 | Murphy et al. |
| 8,372,114 B2 | 2/2013 | Hines |
| 8,377,091 B2 | 2/2013 | Cruise et al. |
| 8,377,112 B2 | 2/2013 | Griffin et al. |
| 8,377,241 B2 | 2/2013 | Farnsworth et al. |
| 8,382,825 B2 | 2/2013 | Garcia et al. |
| 8,388,650 B2 | 3/2013 | Gerberding et al. |
| 8,388,677 B2 | 3/2013 | Herrmann |
| 8,394,136 B2 | 3/2013 | Hartley et al. |
| 8,398,670 B2 | 3/2013 | Amplatz et al. |
| 8,398,701 B2 | 3/2013 | Berez et al. |
| 8,409,267 B2 | 4/2013 | Berez et al. |
| 8,409,269 B2 | 4/2013 | Berez et al. |

(56) References Cited

U.S. PATENT DOCUMENTS

| | | |
|---|---|---|
| 8,414,637 B2 | 4/2013 | Chouinard |
| 8,419,787 B2 | 4/2013 | Yodfat et al. |
| 8,425,541 B2 | 4/2013 | Masters et al. |
| 8,425,542 B2 | 4/2013 | Moftakhar et al. |
| 8,425,548 B2 | 4/2013 | Connor |
| 8,430,922 B2 | 4/2013 | Jung et al. |
| 8,439,942 B2 | 5/2013 | Moran et al. |
| 8,444,667 B2 | 5/2013 | Porter |
| 8,444,668 B2 | 5/2013 | Jones et al. |
| 8,444,686 B2 | 5/2013 | Holman et al. |
| 8,449,532 B2 | 5/2013 | Murphy et al. |
| 8,449,592 B2 | 5/2013 | Wilson et al. |
| 8,454,649 B2 | 6/2013 | Cragg et al. |
| 8,460,240 B2 | 6/2013 | Towler |
| 8,470,013 B2 | 6/2013 | Duggal et al. |
| 8,470,035 B2 | 6/2013 | Cruise et al. |
| 8,473,030 B2 | 6/2013 | Greenan et al. |
| 8,475,517 B2 | 7/2013 | Jung et al. |
| 8,478,437 B2 | 7/2013 | Boyden et al. |
| 8,480,727 B2 | 7/2013 | Clarke |
| 8,486,101 B2 | 7/2013 | Tran et al. |
| 8,491,459 B2 | 7/2013 | Yun |
| 8,491,646 B2 | 7/2013 | Schreck |
| 8,500,788 B2 | 8/2013 | Berez et al. |
| 8,506,618 B2 | 8/2013 | Chouinard et al. |
| 8,506,619 B2 | 8/2013 | Ortiz et al. |
| 8,512,219 B2 | 8/2013 | Ferren et al. |
| 8,512,395 B2 | 8/2013 | Meyer et al. |
| 8,523,934 B2 | 9/2013 | Purdy |
| 8,529,556 B2 | 9/2013 | Murphy et al. |
| 8,529,596 B2 | 9/2013 | Grandfield et al. |
| 8,529,614 B2 | 9/2013 | Berez et al. |
| 8,529,616 B2 | 9/2013 | Boyle et al. |
| 8,529,619 B2 | 9/2013 | Abrams |
| 8,535,367 B2 | 9/2013 | Kim et al. |
| 8,535,590 B2 | 9/2013 | Milner et al. |
| 8,550,344 B2 | 10/2013 | Jung et al. |
| 8,551,155 B2 | 10/2013 | Jung et al. |
| 8,556,953 B2 | 10/2013 | Berez et al. |
| 8,562,636 B2 | 10/2013 | Fogarty et al. |
| 8,562,667 B2 | 10/2013 | Cox |
| 8,577,693 B2 | 11/2013 | Jung et al. |
| 8,597,320 B2 | 12/2013 | Sepetka et al. |
| 8,597,321 B2 | 12/2013 | Monstadt et al. |
| 8,597,323 B1 | 12/2013 | Plaza et al. |
| 8,597,342 B2 | 12/2013 | McKinsey et al. |
| 8,597,745 B2 | 12/2013 | Farnsworth et al. |
| 8,617,132 B2 | 12/2013 | Golzarian et al. |
| 8,623,071 B2 | 1/2014 | Lundkvist et al. |
| 8,636,760 B2 | 1/2014 | Garcia et al. |
| 8,647,377 B2 | 2/2014 | Kim et al. |
| 8,657,865 B2 | 2/2014 | Gumm |
| 8,663,309 B2 | 3/2014 | Chobotov |
| 8,668,716 B2 | 3/2014 | Hines |
| 8,668,717 B2 | 3/2014 | Hines |
| 8,671,815 B2 | 3/2014 | Hancock et al. |
| 8,696,701 B2 | 4/2014 | Becking et al. |
| 8,709,062 B2 | 4/2014 | Dusbabek et al. |
| 8,709,065 B2 | 4/2014 | Chobotov |
| 8,715,312 B2 | 5/2014 | Burke et al. |
| 8,715,317 B1 | 5/2014 | Janardhan et al. |
| 8,715,336 B2 | 5/2014 | Chu et al. |
| 8,721,706 B2 | 5/2014 | Jung et al. |
| 8,728,094 B2 | 5/2014 | Roorda et al. |
| 8,728,145 B2 | 5/2014 | Chuter et al. |
| 8,728,146 B2 | 5/2014 | Gregorich et al. |
| 8,734,502 B2 | 5/2014 | Orr |
| 8,740,966 B2 | 6/2014 | Brocker et al. |
| 8,747,430 B2 | 6/2014 | Porter |
| 8,747,432 B1 | 6/2014 | Janardhan et al. |
| 8,747,455 B2 | 6/2014 | Greenberg |
| 8,747,597 B2 | 6/2014 | Rosqueta et al. |
| 8,753,371 B1 | 6/2014 | Janardhan et al. |
| 8,764,788 B2 | 7/2014 | Martinez |
| 8,769,796 B2 | 7/2014 | Bourang et al. |
| 8,771,294 B2 | 7/2014 | Sepetka et al. |
| 8,771,341 B2 | 7/2014 | Strauss et al. |
| 8,771,342 B2 | 7/2014 | Vardi |
| 8,784,446 B1 | 7/2014 | Janardhan et al. |
| 8,784,475 B2 | 7/2014 | Martinson et al. |
| 8,784,477 B2 | 7/2014 | Bregulla et al. |
| 8,795,345 B2 | 8/2014 | Grandfield et al. |
| 8,795,346 B2 | 8/2014 | Alkhatib |
| 8,795,347 B2 | 8/2014 | Bourang et al. |
| 8,801,772 B2 | 8/2014 | Shobayashi et al. |
| 8,808,347 B2 | 8/2014 | Bourang et al. |
| 8,808,361 B2 | 8/2014 | Strauss et al. |
| 8,813,625 B1 | 8/2014 | Janardhan et al. |
| 8,821,564 B2 | 9/2014 | Schreck et al. |
| 8,828,071 B2 | 9/2014 | Bourang et al. |
| 8,840,867 B2 | 9/2014 | Sophie et al. |
| 8,845,679 B1 | 9/2014 | Janardhan et al. |
| 2001/0000797 A1 | 5/2001 | Mazzocchi |
| 2001/0001835 A1 | 5/2001 | Greene et al. |
| 2001/0009996 A1 | 7/2001 | Ferrera et al. |
| 2001/0016766 A1 | 8/2001 | Vardi et al. |
| 2001/0037137 A1 | 11/2001 | Vardi et al. |
| 2001/0056281 A1 | 12/2001 | Wallace et al. |
| 2002/0002382 A1 | 1/2002 | Wallace et al. |
| 2002/0018752 A1 | 2/2002 | Krall et al. |
| 2002/0042628 A1 | 4/2002 | Chin et al. |
| 2002/0058962 A1 | 5/2002 | Wallace et al. |
| 2002/0082620 A1 | 6/2002 | Lee |
| 2002/0082636 A1 | 6/2002 | Sawhney et al. |
| 2002/0087077 A1 | 7/2002 | Wallace et al. |
| 2002/0107534 A1 | 8/2002 | Schaefer et al. |
| 2002/0116047 A1 | 8/2002 | Vardi et al. |
| 2002/0120276 A1 | 8/2002 | Greene et al. |
| 2002/0128671 A1 | 9/2002 | Wallace et al. |
| 2002/0133190 A1 | 9/2002 | Horton et al. |
| 2002/0143348 A1 | 10/2002 | Wallace et al. |
| 2002/0151926 A1 | 10/2002 | Wallace et al. |
| 2002/0151965 A1 | 10/2002 | Roth |
| 2002/0156516 A1 | 10/2002 | Vardi et al. |
| 2002/0169473 A1 | 11/2002 | Sepetka et al. |
| 2002/0177855 A1 | 11/2002 | Greene et al. |
| 2003/0014007 A1 | 1/2003 | Eidenschink et al. |
| 2003/0014075 A1 | 1/2003 | Rosenbluth et al. |
| 2003/0018294 A1 | 1/2003 | Cox |
| 2003/0018356 A1 | 1/2003 | Schaefer et al. |
| 2003/0065375 A1 | 4/2003 | Eskuri |
| 2003/0074049 A1 | 4/2003 | Hoganson et al. |
| 2003/0074056 A1 | 4/2003 | Killion et al. |
| 2003/0083676 A1 | 5/2003 | Wallace |
| 2003/0083737 A1 | 5/2003 | Greene et al. |
| 2003/0088311 A1 | 5/2003 | Greene et al. |
| 2003/0093097 A1 | 5/2003 | Avellanet et al. |
| 2003/0093108 A1 | 5/2003 | Avellanet et al. |
| 2003/0093111 A1 | 5/2003 | Ken et al. |
| 2003/0100945 A1 | 5/2003 | Yodfat et al. |
| 2003/0109917 A1 | 6/2003 | Rudin et al. |
| 2003/0130689 A1 | 7/2003 | Wallace et al. |
| 2003/0135264 A1 | 7/2003 | Whalen et al. |
| 2003/0139802 A1* | 7/2003 | Wulfman ......... A61B 17/12022 623/1.15 |
| 2003/0159920 A1 | 8/2003 | Roth |
| 2003/0181927 A1 | 9/2003 | Wallace |
| 2003/0187473 A1 | 10/2003 | Berenstein et al. |
| 2003/0195553 A1 | 10/2003 | Wallace et al. |
| 2003/0195606 A1 | 10/2003 | Davidson et al. |
| 2003/0223955 A1 | 12/2003 | Whalen et al. |
| 2004/0002752 A1 | 1/2004 | Griffin et al. |
| 2004/0015227 A1 | 1/2004 | Vardi et al. |
| 2004/0045554 A1 | 3/2004 | Schaefer et al. |
| 2004/0059370 A1 | 3/2004 | Greene et al. |
| 2004/0091543 A1 | 5/2004 | Bell et al. |
| 2004/0093014 A1 | 5/2004 | Ho et al. |
| 2004/0098027 A1 | 5/2004 | Teoh et al. |
| 2004/0098028 A1 | 5/2004 | Martinez |
| 2004/0111112 A1 | 6/2004 | Hoffmann |
| 2004/0111142 A1 | 6/2004 | Rourke et al. |
| 2004/0115164 A1 | 6/2004 | Pierce et al. |
| 2004/0158282 A1 | 8/2004 | Jones et al. |
| 2004/0161451 A1 | 8/2004 | Pierce et al. |

(56) References Cited

U.S. PATENT DOCUMENTS

| | | |
|---|---|---|
| 2004/0181253 A1 | 9/2004 | Sepetka et al. |
| 2004/0186551 A1 | 9/2004 | Kao et al. |
| 2004/0193246 A1 | 9/2004 | Ferrera |
| 2004/0210249 A1 | 10/2004 | Fogarty et al. |
| 2004/0215331 A1 | 10/2004 | Chew et al. |
| 2004/0220663 A1 | 11/2004 | Rivelli, Jr. |
| 2004/0243168 A1 | 12/2004 | Ferrera et al. |
| 2004/0243216 A1 | 12/2004 | Gregorich |
| 2004/0249435 A1 | 12/2004 | Andreas et al. |
| 2004/0249439 A1 | 12/2004 | Richter et al. |
| 2004/0260384 A1 | 12/2004 | Allen |
| 2005/0004660 A1 | 1/2005 | Rosenbluth et al. |
| 2005/0010281 A1 | 1/2005 | Yodfat et al. |
| 2005/0015110 A1 | 1/2005 | Fogarty et al. |
| 2005/0021077 A1 | 1/2005 | Chin et al. |
| 2005/0033349 A1 | 2/2005 | Jones et al. |
| 2005/0033350 A1 | 2/2005 | Ken et al. |
| 2005/0065592 A1 | 3/2005 | Holzer |
| 2005/0075405 A1 | 4/2005 | Wilson et al. |
| 2005/0080445 A1 | 4/2005 | Sawhney et al. |
| 2005/0090888 A1 | 4/2005 | Hines et al. |
| 2005/0095428 A1 | 5/2005 | Dicarlo et al. |
| 2005/0096728 A1 | 5/2005 | Ramer |
| 2005/0107863 A1 | 5/2005 | Brown |
| 2005/0119687 A1 | 6/2005 | Dacey et al. |
| 2005/0131516 A1 | 6/2005 | Greenhalgh |
| 2005/0131518 A1 | 6/2005 | Hartley et al. |
| 2005/0133046 A1 | 6/2005 | Becker et al. |
| 2005/0149159 A1 | 7/2005 | Andreas et al. |
| 2005/0149164 A1 | 7/2005 | Rivelli |
| 2005/0171572 A1 | 8/2005 | Martinez |
| 2005/0171597 A1 | 8/2005 | Boatman et al. |
| 2005/0192618 A1 | 9/2005 | Porter |
| 2005/0192621 A1 | 9/2005 | Wallace et al. |
| 2005/0192661 A1 | 9/2005 | Griffen et al. |
| 2005/0209674 A1 | 9/2005 | Kutscher et al. |
| 2005/0228434 A1 | 10/2005 | Amplatz et al. |
| 2005/0251247 A1 | 11/2005 | Roth |
| 2005/0267510 A1 | 12/2005 | Razack |
| 2005/0267568 A1 | 12/2005 | Berez et al. |
| 2005/0277978 A1 | 12/2005 | Greenhalgh |
| 2005/0283220 A1 | 12/2005 | Gobran et al. |
| 2006/0036045 A1 | 2/2006 | Wilson et al. |
| 2006/0036281 A1 | 2/2006 | Patterson et al. |
| 2006/0052816 A1 | 3/2006 | Bates et al. |
| 2006/0058834 A1 | 3/2006 | Do et al. |
| 2006/0079923 A1 | 4/2006 | Chhabra et al. |
| 2006/0085061 A1 | 4/2006 | Vardi et al. |
| 2006/0116709 A1 | 6/2006 | Sepetka et al. |
| 2006/0116712 A1 | 6/2006 | Sepetka et al. |
| 2006/0116713 A1 | 6/2006 | Sepetka et al. |
| 2006/0136033 A1 | 6/2006 | Hermann et al. |
| 2006/0149299 A1 | 7/2006 | Greene et al. |
| 2006/0155323 A1 | 7/2006 | Porter et al. |
| 2006/0155367 A1* | 7/2006 | Hines ............ A61F 2/844 623/1.28 |
| 2006/0184195 A1 | 8/2006 | Schaefer et al. |
| 2006/0184196 A1 | 8/2006 | Schaefer et al. |
| 2006/0206196 A1 | 9/2006 | Porter |
| 2006/0206200 A1 | 9/2006 | Garcia et al. |
| 2006/0206201 A1 | 9/2006 | Garcia et al. |
| 2006/0224230 A1 | 10/2006 | Rivelli et al. |
| 2006/0229714 A1 | 10/2006 | Lombardi et al. |
| 2006/0235464 A1 | 10/2006 | Avellanet et al. |
| 2006/0241690 A1 | 10/2006 | Amplatz et al. |
| 2006/0241740 A1 | 10/2006 | Vardi et al. |
| 2006/0251695 A1 | 11/2006 | Henson et al. |
| 2006/0251700 A1 | 11/2006 | Henson et al. |
| 2006/0271149 A1 | 11/2006 | Berez et al. |
| 2006/0271153 A1 | 11/2006 | Garcia et al. |
| 2006/0276831 A1 | 12/2006 | Porter et al. |
| 2006/0292206 A1 | 12/2006 | Kim et al. |
| 2007/0016233 A1 | 1/2007 | Ferrera et al. |
| 2007/0021816 A1 | 1/2007 | Rudin |
| 2007/0031584 A1 | 2/2007 | Roth |
| 2007/0032855 A1 | 2/2007 | Davidson et al. |
| 2007/0050008 A1 | 3/2007 | Kim et al. |
| 2007/0055355 A1 | 3/2007 | Kim et al. |
| 2007/0060994 A1 | 3/2007 | Gobran et al. |
| 2007/0061005 A1 | 3/2007 | Kim et al. |
| 2007/0067015 A1 | 3/2007 | Jones et al. |
| 2007/0083257 A1 | 4/2007 | Pal et al. |
| 2007/0088368 A1 | 4/2007 | Acosta et al. |
| 2007/0088387 A1 | 4/2007 | Eskridge et al. |
| 2007/0100301 A1 | 5/2007 | Gumm |
| 2007/0106311 A1 | 5/2007 | Wallace et al. |
| 2007/0129786 A1 | 6/2007 | Beach et al. |
| 2007/0135907 A1 | 6/2007 | Wilson et al. |
| 2007/0150041 A1 | 6/2007 | Evans et al. |
| 2007/0150045 A1 | 6/2007 | Ferrera |
| 2007/0167747 A1 | 7/2007 | Borgert et al. |
| 2007/0175536 A1 | 8/2007 | Monetti et al. |
| 2007/0176333 A1 | 8/2007 | Greene et al. |
| 2007/0207186 A1 | 9/2007 | Scanlon et al. |
| 2007/0219578 A1 | 9/2007 | Solar et al. |
| 2007/0219610 A1 | 9/2007 | Israel |
| 2007/0219619 A1 | 9/2007 | Dieck et al. |
| 2007/0225794 A1 | 9/2007 | Thramann et al. |
| 2007/0239261 A1 | 10/2007 | Bose et al. |
| 2007/0265656 A1 | 11/2007 | Amplatz et al. |
| 2007/0299464 A1 | 12/2007 | Cruise et al. |
| 2007/0299498 A1 | 12/2007 | Perez et al. |
| 2008/0004653 A1 | 1/2008 | Sherman et al. |
| 2008/0004692 A1 | 1/2008 | Henson et al. |
| 2008/0031919 A1 | 2/2008 | Henson et al. |
| 2008/0033341 A1 | 2/2008 | Grad |
| 2008/0033366 A1 | 2/2008 | Matson et al. |
| 2008/0039933 A1 | 2/2008 | Yodfat et al. |
| 2008/0097495 A1 | 4/2008 | Feller et al. |
| 2008/0103585 A1 | 5/2008 | Monstadt et al. |
| 2008/0114391 A1 | 5/2008 | Dieck et al. |
| 2008/0114436 A1 | 5/2008 | Dieck et al. |
| 2008/0125852 A1 | 5/2008 | Garrison et al. |
| 2008/0147100 A1 | 6/2008 | Wallace |
| 2008/0152686 A1 | 6/2008 | Henson et al. |
| 2008/0161936 A1 | 7/2008 | Feller et al. |
| 2008/0195137 A1 | 8/2008 | Alleyne et al. |
| 2008/0200945 A1 | 8/2008 | Amplatz et al. |
| 2008/0221600 A1 | 9/2008 | Dieck et al. |
| 2008/0249608 A1 | 10/2008 | Dave |
| 2008/0281350 A1 | 11/2008 | Sepetka et al. |
| 2008/0312732 A1 | 12/2008 | Hartley et al. |
| 2008/0319521 A1 | 12/2008 | Norris et al. |
| 2008/0319525 A1 | 12/2008 | Tieu et al. |
| 2008/0319533 A1 | 12/2008 | Lehe |
| 2009/0062834 A1 | 3/2009 | Moftakhar et al. |
| 2009/0062841 A1 | 3/2009 | Amplatz et al. |
| 2009/0069880 A1 | 3/2009 | Vonderwalde et al. |
| 2009/0082846 A1 | 3/2009 | Chobotov |
| 2009/0088832 A1 | 4/2009 | Chew et al. |
| 2009/0105748 A1 | 4/2009 | Fogarty et al. |
| 2009/0112249 A1 | 4/2009 | Miles et al. |
| 2009/0112250 A1 | 4/2009 | Greene et al. |
| 2009/0118761 A1 | 5/2009 | Masters et al. |
| 2009/0125053 A1 | 5/2009 | Ferrera et al. |
| 2009/0132028 A1 | 5/2009 | Vardi et al. |
| 2009/0149864 A1 | 6/2009 | Porter |
| 2009/0164013 A1 | 6/2009 | Cruise et al. |
| 2009/0171437 A1 | 7/2009 | Brocker et al. |
| 2009/0177268 A1 | 7/2009 | Lundkvist et al. |
| 2009/0192536 A1 | 7/2009 | Berez et al. |
| 2009/0198318 A1 | 8/2009 | Berez et al. |
| 2009/0227976 A1 | 9/2009 | Calabria et al. |
| 2009/0228029 A1 | 9/2009 | Lee |
| 2009/0232869 A1 | 9/2009 | Greene et al. |
| 2009/0248135 A1 | 10/2009 | Bruszewski et al. |
| 2009/0254111 A1 | 10/2009 | Monstadt et al. |
| 2009/0270970 A1 | 10/2009 | Yodfat et al. |
| 2009/0270974 A1 | 10/2009 | Berez et al. |
| 2009/0275974 A1 | 11/2009 | Marchand et al. |
| 2009/0287241 A1 | 11/2009 | Berez et al. |
| 2009/0287288 A1 | 11/2009 | Berez et al. |
| 2009/0287291 A1 | 11/2009 | Becking et al. |
| 2009/0287292 A1 | 11/2009 | Becking et al. |

(56) References Cited

U.S. PATENT DOCUMENTS

| | | |
|---|---|---|
| 2009/0287294 A1 | 11/2009 | Rosqueta et al. |
| 2009/0292348 A1 | 11/2009 | Berez et al. |
| 2009/0297582 A1 | 12/2009 | Meyer et al. |
| 2009/0299326 A1 | 12/2009 | Morsi |
| 2009/0299390 A1 | 12/2009 | Dehnad |
| 2009/0299448 A1 | 12/2009 | Timko et al. |
| 2009/0318941 A1 | 12/2009 | Sepetka et al. |
| 2009/0318947 A1 | 12/2009 | Garcia et al. |
| 2009/0318948 A1 | 12/2009 | Linder et al. |
| 2009/0318949 A1 | 12/2009 | Ganpath et al. |
| 2009/0319017 A1 | 12/2009 | Berez et al. |
| 2009/0319023 A1 | 12/2009 | Hildebrand et al. |
| 2010/0004671 A1 | 1/2010 | Gerberding et al. |
| 2010/0004726 A1 | 1/2010 | Hancock et al. |
| 2010/0010624 A1 | 1/2010 | Berez et al. |
| 2010/0016833 A1 | 1/2010 | Ogle et al. |
| 2010/0023105 A1 | 1/2010 | Levy et al. |
| 2010/0036412 A1 | 2/2010 | Porter et al. |
| 2010/0042200 A1 | 2/2010 | Richter et al. |
| 2010/0063472 A1 | 3/2010 | Becker et al. |
| 2010/0063531 A1 | 3/2010 | Rudakov et al. |
| 2010/0069948 A1 | 3/2010 | Veznedaroglu et al. |
| 2010/0082091 A1 | 4/2010 | Berez et al. |
| 2010/0094335 A1 | 4/2010 | Gerberding et al. |
| 2010/0106240 A1 | 4/2010 | Duggal et al. |
| 2010/0114302 A1 | 5/2010 | Tzafriri et al. |
| 2010/0131002 A1 | 5/2010 | Connor et al. |
| 2010/0152828 A1 | 6/2010 | Pakbaz et al. |
| 2010/0152834 A1 | 6/2010 | Hannes et al. |
| 2010/0152837 A1 | 6/2010 | Lundkvist et al. |
| 2010/0168781 A1 | 7/2010 | Berenstein et al. |
| 2010/0174301 A1 | 7/2010 | Wallace et al. |
| 2010/0179640 A1 | 7/2010 | Reith |
| 2010/0179645 A1 | 7/2010 | Chen et al. |
| 2010/0198250 A1 | 8/2010 | Ricci et al. |
| 2010/0198334 A1 | 8/2010 | Yodfat et al. |
| 2010/0222804 A1 | 9/2010 | Murphy et al. |
| 2010/0222864 A1 | 9/2010 | Rivelli et al. |
| 2010/0274276 A1 | 10/2010 | Chow et al. |
| 2010/0274346 A1 | 10/2010 | Chouinard et al. |
| 2010/0280452 A1 | 11/2010 | Chen et al. |
| 2010/0305681 A1 | 12/2010 | Gumm |
| 2010/0312326 A1 | 12/2010 | Chuter et al. |
| 2010/0318173 A1 | 12/2010 | Kolandaivelu et al. |
| 2010/0324660 A1 | 12/2010 | Denison |
| 2011/0004294 A1 | 1/2011 | Bialas |
| 2011/0005062 A1 | 1/2011 | Greene et al. |
| 2011/0009940 A1 | 1/2011 | Grandfield et al. |
| 2011/0009941 A1 | 1/2011 | Grandfield et al. |
| 2011/0009950 A1 | 1/2011 | Grandfield et al. |
| 2011/0022149 A1 | 1/2011 | Cox et al. |
| 2011/0039967 A1 | 2/2011 | Wilson et al. |
| 2011/0046658 A1 | 2/2011 | Connor et al. |
| 2011/0046716 A1 | 2/2011 | Parkinson et al. |
| 2011/0054511 A1 | 3/2011 | Henson et al. |
| 2011/0054589 A1 | 3/2011 | Bashiri et al. |
| 2011/0066221 A1 | 3/2011 | White et al. |
| 2011/0082427 A1 | 4/2011 | Golzarian et al. |
| 2011/0082491 A1 | 4/2011 | Sepetka et al. |
| 2011/0082533 A1 | 4/2011 | Vardi et al. |
| 2011/0089592 A1 | 4/2011 | Farnsworth et al. |
| 2011/0092997 A1 | 4/2011 | Kang |
| 2011/0098814 A1 | 4/2011 | Monstadt et al. |
| 2011/0118777 A1 | 5/2011 | Patterson et al. |
| 2011/0137332 A1 | 6/2011 | Sepetka et al. |
| 2011/0137405 A1 | 6/2011 | Wilson et al. |
| 2011/0144669 A1 | 6/2011 | Becking et al. |
| 2011/0144686 A1 | 6/2011 | Wilson et al. |
| 2011/0144740 A1 | 6/2011 | Molaei et al. |
| 2011/0152993 A1 | 6/2011 | Marchand et al. |
| 2011/0152996 A1 | 6/2011 | Acosta et al. |
| 2011/0152998 A1 | 6/2011 | Berez et al. |
| 2011/0166588 A1 | 7/2011 | Connor et al. |
| 2011/0166592 A1 | 7/2011 | Garcia et al. |
| 2011/0166641 A1 | 7/2011 | Bales et al. |
| 2011/0182998 A1 | 7/2011 | Reb et al. |
| 2011/0184451 A1 | 7/2011 | Sahl |
| 2011/0184452 A1 | 7/2011 | Huynh et al. |
| 2011/0184453 A1 | 7/2011 | Levy et al. |
| 2011/0184454 A1 | 7/2011 | Barry et al. |
| 2011/0184455 A1 | 7/2011 | Keeley et al. |
| 2011/0184456 A1 | 7/2011 | Grandfield et al. |
| 2011/0196413 A1 | 8/2011 | Wallace et al. |
| 2011/0202085 A1 | 8/2011 | Loganathan et al. |
| 2011/0208227 A1 | 8/2011 | Becking |
| 2011/0213406 A1 | 9/2011 | Aganon et al. |
| 2011/0224776 A1 | 9/2011 | Sepetka et al. |
| 2011/0230957 A1 | 9/2011 | Bonsignore et al. |
| 2011/0238105 A1 | 9/2011 | Gelbart et al. |
| 2011/0245862 A1 | 10/2011 | Dieck et al. |
| 2011/0245863 A1 | 10/2011 | Martinez |
| 2011/0264192 A1 | 10/2011 | Hartley et al. |
| 2011/0265943 A1 | 11/2011 | Rosqueta et al. |
| 2011/0276071 A1 | 11/2011 | Connor et al. |
| 2011/0282378 A1 | 11/2011 | Murphy et al. |
| 2011/0286925 A1 | 11/2011 | Lerouge et al. |
| 2011/0288627 A1 | 11/2011 | Hartley et al. |
| 2011/0307044 A1 | 12/2011 | Bourang et al. |
| 2011/0307045 A1 | 12/2011 | Bourang et al. |
| 2011/0307046 A1 | 12/2011 | Bourang et al. |
| 2011/0307052 A1 | 12/2011 | Bourang et al. |
| 2011/0313443 A1 | 12/2011 | Lorenzo et al. |
| 2011/0313512 A1 | 12/2011 | Hartley et al. |
| 2011/0319926 A1 | 12/2011 | Becking et al. |
| 2011/0319928 A1 | 12/2011 | Griffin et al. |
| 2012/0004682 A1 | 1/2012 | Connor |
| 2012/0004719 A1 | 1/2012 | Gregorich et al. |
| 2012/0016462 A1 | 1/2012 | Gregorich et al. |
| 2012/0041540 A1 | 2/2012 | Shobayashi et al. |
| 2012/0046676 A1 | 2/2012 | Morsi |
| 2012/0053670 A1 | 3/2012 | Purdy |
| 2012/0055614 A1 | 3/2012 | Hancock et al. |
| 2012/0071911 A1 | 3/2012 | Sadasivan et al. |
| 2012/0078285 A1 | 3/2012 | Griffin |
| 2012/0089174 A1 | 4/2012 | Chen et al. |
| 2012/0116352 A1 | 5/2012 | Rangi |
| 2012/0116441 A1 | 5/2012 | Yamanaka et al. |
| 2012/0116442 A1 | 5/2012 | Monstadt et al. |
| 2012/0130479 A1 | 5/2012 | Chuter et al. |
| 2012/0143237 A1 | 6/2012 | Cam et al. |
| 2012/0143317 A1 | 6/2012 | Cam et al. |
| 2012/0165919 A1 | 6/2012 | Cox et al. |
| 2012/0165920 A1 | 6/2012 | Meyer et al. |
| 2012/0172921 A1 | 7/2012 | Yamanaka et al. |
| 2012/0172972 A1 | 7/2012 | Meyer et al. |
| 2012/0172977 A1 | 7/2012 | Bregulla et al. |
| 2012/0179192 A1 | 7/2012 | Fogarty et al. |
| 2012/0197283 A1 | 8/2012 | Marchand et al. |
| 2012/0209309 A1 | 8/2012 | Chen et al. |
| 2012/0209311 A1 | 8/2012 | Grandfield et al. |
| 2012/0215250 A1 | 8/2012 | Grandfield et al. |
| 2012/0221095 A1 | 8/2012 | Berez et al. |
| 2012/0238644 A1 | 9/2012 | Gong et al. |
| 2012/0239074 A1 | 9/2012 | Aboytes et al. |
| 2012/0245674 A1 | 9/2012 | Molaei et al. |
| 2012/0245675 A1 | 9/2012 | Molaei et al. |
| 2012/0253369 A1 | 10/2012 | Morsi |
| 2012/0253377 A1 | 10/2012 | Slazas et al. |
| 2012/0253448 A1 | 10/2012 | Hartley et al. |
| 2012/0259354 A1 | 10/2012 | Kellett |
| 2012/0259404 A1 | 10/2012 | Tieu et al. |
| 2012/0265287 A1 | 10/2012 | Sharma et al. |
| 2012/0271200 A1 | 10/2012 | Martinson et al. |
| 2012/0271399 A1 | 10/2012 | Perkins et al. |
| 2012/0277784 A1 | 11/2012 | Berez et al. |
| 2012/0283764 A1 | 11/2012 | Solar et al. |
| 2012/0283765 A1 | 11/2012 | Berez et al. |
| 2012/0283768 A1 | 11/2012 | Cox et al. |
| 2012/0283769 A1 | 11/2012 | Cruise et al. |
| 2012/0283815 A1 | 11/2012 | Berez et al. |
| 2012/0289995 A1 | 11/2012 | Constant et al. |
| 2012/0296361 A1 | 11/2012 | Cam et al. |
| 2012/0296362 A1 | 11/2012 | Cam et al. |
| 2012/0303052 A1 | 11/2012 | Connor |

(56) References Cited

U.S. PATENT DOCUMENTS

| | | |
|---|---|---|
| 2012/0303108 A1 | 11/2012 | Fogarty et al. |
| 2012/0303112 A1 | 11/2012 | Armstrong et al. |
| 2012/0310270 A1 | 12/2012 | Murphy et al. |
| 2012/0310271 A1 | 12/2012 | Kwon |
| 2012/0310611 A1 | 12/2012 | Sadasivan et al. |
| 2012/0316598 A1 | 12/2012 | Becking et al. |
| 2012/0316632 A1 | 12/2012 | Gao |
| 2012/0316638 A1 | 12/2012 | Grad et al. |
| 2012/0323268 A1 | 12/2012 | Martinez |
| 2012/0323309 A1 | 12/2012 | Cattaneo |
| 2012/0323547 A1 | 12/2012 | Baloch et al. |
| 2012/0330341 A1 | 12/2012 | Becking et al. |
| 2012/0330343 A1 | 12/2012 | Kim et al. |
| 2012/0330347 A1 | 12/2012 | Becking et al. |
| 2012/0330402 A1 | 12/2012 | Vad et al. |
| 2013/0012979 A1 | 1/2013 | Amplatz et al. |
| 2013/0018220 A1 | 1/2013 | Vad et al. |
| 2013/0018409 A1 | 1/2013 | Le et al. |
| 2013/0023903 A1 | 1/2013 | Roorda et al. |
| 2013/0035712 A1 | 2/2013 | Theobald et al. |
| 2013/0041454 A1 | 2/2013 | Dobson et al. |
| 2013/0045182 A1 | 2/2013 | Gong et al. |
| 2013/0046371 A1 | 2/2013 | Greenberg et al. |
| 2013/0053872 A1 | 2/2013 | Hansen |
| 2013/0053944 A1 | 2/2013 | Welch |
| 2013/0060317 A1 | 3/2013 | Dusbabek et al. |
| 2013/0060322 A1 | 3/2013 | Leynov et al. |
| 2013/0066357 A1 | 3/2013 | Aboytes et al. |
| 2013/0066359 A1 | 3/2013 | Murphy et al. |
| 2013/0066360 A1 | 3/2013 | Becking et al. |
| 2013/0066413 A1 | 3/2013 | Jin et al. |
| 2013/0066415 A1 | 3/2013 | Hocking |
| 2013/0072959 A1 | 3/2013 | Wu et al. |
| 2013/0085518 A1 | 4/2013 | Trommeter et al. |
| 2013/0085522 A1 | 4/2013 | Becking et al. |
| 2013/0089576 A1 | 4/2013 | Maitland et al. |
| 2013/0090682 A1 | 4/2013 | Bachman et al. |
| 2013/0090719 A1 | 4/2013 | Bales et al. |
| 2013/0090721 A1 | 4/2013 | Bales et al. |
| 2013/0095087 A1 | 4/2013 | Shalaby et al. |
| 2013/0103074 A1 | 4/2013 | Riina et al. |
| 2013/0103135 A1 | 4/2013 | Vinluan |
| 2013/0108574 A1 | 5/2013 | Chevalier et al. |
| 2013/0116659 A1 | 5/2013 | Porter |
| 2013/0116722 A1 | 5/2013 | Aboytes et al. |
| 2013/0116774 A1 | 5/2013 | Strauss et al. |
| 2013/0123830 A1 | 5/2013 | Becking et al. |
| 2013/0123899 A1 | 5/2013 | Leopold et al. |
| 2013/0123901 A1 | 5/2013 | Connor et al. |
| 2013/0131711 A1 | 5/2013 | Bowman |
| 2013/0131716 A1 | 5/2013 | Cruise et al. |
| 2013/0131780 A1 | 5/2013 | Armstrong et al. |
| 2013/0131786 A1 | 5/2013 | Chobotov |
| 2013/0146173 A1 | 6/2013 | Krivoruchko et al. |
| 2013/0150946 A1 | 6/2013 | Hartley et al. |
| 2013/0166010 A1 | 6/2013 | Vad |
| 2013/0166017 A1 | 6/2013 | Cartledge et al. |
| 2013/0172925 A1 | 7/2013 | Garcia et al. |
| 2013/0172975 A1 | 7/2013 | Berez et al. |
| 2013/0172976 A1 | 7/2013 | Garcia et al. |
| 2013/0190795 A1 | 7/2013 | Matson et al. |
| 2013/0190800 A1 | 7/2013 | Murphy et al. |
| 2013/0190805 A1 | 7/2013 | Slazas et al. |
| 2013/0197547 A1 | 8/2013 | Fukuoka et al. |
| 2013/0197570 A1 | 8/2013 | Ebata et al. |
| 2013/0197617 A1 | 8/2013 | Armstrong et al. |
| 2013/0197624 A1 | 8/2013 | Armstrong et al. |
| 2013/0204288 A1 | 8/2013 | Johnson et al. |
| 2013/0204289 A1 | 8/2013 | Dasnurkar et al. |
| 2013/0204290 A1 | 8/2013 | Clarke et al. |
| 2013/0204347 A1 | 8/2013 | Armstrong et al. |
| 2013/0204351 A1 | 8/2013 | Cox et al. |
| 2013/0204354 A1 | 8/2013 | Adams |
| 2013/0211443 A1 | 8/2013 | Cragg et al. |
| 2013/0211492 A1 | 8/2013 | Schneider et al. |
| 2013/0211497 A1 | 8/2013 | Charlebois et al. |
| 2013/0211498 A1 | 8/2013 | Buckley et al. |
| 2013/0211505 A1 | 8/2013 | Robison |
| 2013/0211507 A1 | 8/2013 | LaDuca et al. |
| 2013/0218191 A1 | 8/2013 | Heltai |
| 2013/0226276 A1 | 8/2013 | Newell et al. |
| 2013/0226278 A1 | 8/2013 | Newell et al. |
| 2013/0231695 A1 | 9/2013 | Malek |
| 2013/0231732 A1 | 9/2013 | Vonderwalde et al. |
| 2013/0238083 A1 | 9/2013 | Duggal et al. |
| 2013/0245606 A1 | 9/2013 | Stam et al. |
| 2013/0245667 A1 | 9/2013 | Marchand et al. |
| 2013/0245745 A1 | 9/2013 | Vong et al. |
| 2013/0252900 A1 | 9/2013 | Reb et al. |
| 2013/0253086 A1 | 9/2013 | Wilson et al. |
| 2013/0253572 A1 | 9/2013 | Molaei et al. |
| 2013/0253631 A1 | 9/2013 | Schmid et al. |
| 2013/0253634 A1 | 9/2013 | Wilson et al. |
| 2013/0261728 A1 | 10/2013 | Perkins et al. |
| 2013/0261730 A1 | 10/2013 | Bose et al. |
| 2013/0261732 A1 | 10/2013 | Perkins et al. |
| 2013/0267986 A1 | 10/2013 | Hines |
| 2013/0268046 A1 | 10/2013 | Gerberding et al. |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0282096 A1 | 10/2013 | Berez et al. |
| 2013/0289690 A1 | 10/2013 | Thapliyal |
| 2013/0289713 A1 | 10/2013 | Pearson et al. |
| 2013/0289714 A1 | 10/2013 | Strauss et al. |
| 2013/0302251 A1 | 11/2013 | Constant et al. |
| 2013/0304109 A1 | 11/2013 | Abrams et al. |
| 2013/0310687 A1 | 11/2013 | Takizawa et al. |
| 2013/0325053 A1 | 12/2013 | Porter et al. |
| 2013/0331883 A1 | 12/2013 | Strauss et al. |
| 2013/0338688 A1 | 12/2013 | Rehman et al. |
| 2013/0344159 A1 | 12/2013 | Moine et al. |
| 2013/0345738 A1 | 12/2013 | Eskridge |
| 2013/0345785 A1 | 12/2013 | Hartley et al. |
| 2014/0005698 A1 | 1/2014 | Eskridge |
| 2014/0012303 A1 | 1/2014 | Heipl |
| 2014/0012307 A1 | 1/2014 | Franano et al. |
| 2014/0012363 A1 | 1/2014 | Franano et al. |
| 2014/0018843 A1 | 1/2014 | Berez et al. |
| 2014/0018902 A1 | 1/2014 | Myr |
| 2014/0025151 A1 | 1/2014 | Gao |
| 2014/0025154 A1 | 1/2014 | Liang et al. |
| 2014/0031858 A1 | 1/2014 | Bhagchandani et al. |
| 2014/0031918 A1 | 1/2014 | Newell et al. |
| 2014/0031920 A1 | 1/2014 | Malek |
| 2014/0039536 A1 | 2/2014 | Cully et al. |
| 2014/0039606 A1 | 2/2014 | Rudakov et al. |
| 2014/0046338 A1 | 2/2014 | Grandfield et al. |
| 2014/0047694 A1 | 2/2014 | Monstadt et al. |
| 2014/0052168 A1 | 2/2014 | Sawhney |
| 2014/0052233 A1 | 2/2014 | Cox et al. |
| 2014/0058420 A1 | 2/2014 | Hannes et al. |
| 2014/0058436 A1 | 2/2014 | Rosenbluth et al. |
| 2014/0058498 A1 | 2/2014 | Hannes et al. |
| 2014/0058500 A1 | 2/2014 | Lundkvist et al. |
| 2014/0074149 A1 | 3/2014 | Garcia et al. |
| 2014/0081313 A1 | 3/2014 | Elliott |
| 2014/0081374 A1 | 3/2014 | Kim et al. |
| 2014/0082924 A1 | 3/2014 | Lundkvist et al. |
| 2014/0083969 A1 | 3/2014 | Porter |
| 2014/0088690 A1 | 3/2014 | Fogarty et al. |
| 2014/0094896 A1 | 4/2014 | Berez et al. |
| 2014/0099374 A1 | 4/2014 | Golzarian et al. |
| 2014/0100647 A1 | 4/2014 | Bourang |
| 2014/0114342 A1 | 4/2014 | Berez et al. |
| 2014/0114343 A1 | 4/2014 | Lee et al. |
| 2014/0121744 A1 | 5/2014 | Kusleika |
| 2014/0121745 A1 | 5/2014 | Kusleika et al. |
| 2014/0121746 A1 | 5/2014 | Kusleika et al. |
| 2014/0121752 A1 | 5/2014 | Losordo et al. |
| 2014/0128901 A1 | 5/2014 | Kang et al. |
| 2014/0128907 A1 | 5/2014 | Hui et al. |

(56) References Cited

U.S. PATENT DOCUMENTS

| | | |
|---|---|---|
| 2014/0128957 A1 | 5/2014 | Losordo et al. |
| 2014/0130965 A1 | 5/2014 | Banks et al. |
| 2014/0135810 A1 | 5/2014 | Divino et al. |
| 2014/0135811 A1 | 5/2014 | Divino et al. |
| 2014/0135812 A1 | 5/2014 | Divino et al. |
| 2014/0142611 A1 | 5/2014 | Plaza et al. |
| 2014/0163604 A1 | 6/2014 | Monstadt |
| 2014/0172001 A1 | 6/2014 | Becking et al. |
| 2014/0172067 A1 | 6/2014 | Brown et al. |
| 2014/0172071 A1 | 6/2014 | Berez et al. |
| 2014/0180377 A1 | 6/2014 | Bose et al. |
| 2014/0180387 A1 | 6/2014 | Khenansho et al. |
| 2014/0180397 A1 | 6/2014 | Gerberding et al. |
| 2014/0188208 A1 | 7/2014 | Hancock et al. |
| 2014/0194973 A1 | 7/2014 | Chobotov |
| 2014/0200607 A1 | 7/2014 | Sepetka et al. |
| 2014/0200648 A1 | 7/2014 | Newell et al. |
| 2014/0207162 A1 | 7/2014 | Tran et al. |
| 2014/0207180 A1 | 7/2014 | Ferrera |
| 2014/0214071 A1 | 7/2014 | Thomas |
| 2014/0222128 A1 | 8/2014 | Dusbabek et al. |
| 2014/0222130 A1 | 8/2014 | Kusleika |
| 2014/0236216 A1 | 8/2014 | Gerberding |
| 2014/0243951 A1 | 8/2014 | Orr |
| 2014/0249614 A1 | 9/2014 | Levi et al. |
| 2014/0249616 A1 | 9/2014 | Strauss et al. |
| 2014/0249620 A1 | 9/2014 | Carman et al. |
| 2014/0260928 A1 | 9/2014 | Janardhan et al. |
| 2014/0265096 A1 | 9/2014 | Janardhan et al. |
| 2014/0277100 A1 | 9/2014 | Kang |
| 2014/0277361 A1 | 9/2014 | Farhat et al. |
| 2014/0277370 A1 | 9/2014 | Brocker et al. |
| 2014/0277391 A1 | 9/2014 | Layman et al. |
| 2014/0288633 A1 | 9/2014 | Burke et al. |
| 2014/0296358 A1 | 10/2014 | Maitland et al. |

OTHER PUBLICATIONS

U.S. Appl. No. 13/889,451, filed 2013, Connor et al.

\* cited by examiner

STENT WITH OUTER MEMBER TO EMBOLIZE AN ANEURYSM

CROSS-REFERENCE TO RELATED APPLICATIONS

This application is a continuation-in-part of U.S. patent application Ser. No. 12/592,116—entitled "Stent with a Net Layer to Embolize an Aneurysm" filed on Nov. 18, 2009 by Robert Connor and Muhammad Tariq Janjua—the entirety of which is incorporated by reference.

FEDERALLY SPONSORED RESEARCH

Not Applicable

SEQUENCE LISTING OR PROGRAM

Not Applicable

BACKGROUND

1. Field of Invention

This invention relates to devices to treat aneurysms.

2. Background and Review of Related Art

An aneurysm is an abnormal bulging or ballooning of a blood vessel. Rupture of brain aneurysms can cause stroke, death, or disability. Around one-third of people who have a brain aneurysm that ruptures will die within 30 days of the rupture. Of the survivors, around half of them suffer some permanent loss of brain function. Many aneurysms are not identified until they rupture. However, identification of intact aneurysms is increasing due to increased outpatient imaging. Ruptured aneurysms must be treated to stop the bleeding or to prevent re-bleeding. Intact aneurysms may or may not be treated to prevent rupture, depending on their characteristics. Wide neck aneurysms are less prone to rupture, but are harder to treat. In the U.S., it has been estimated that over 10 million people have brain aneurysms and 30,000 people each year have a brain aneurysm that ruptures.

Several approaches can be used to treat brain aneurysms. These different approaches can be divided into three categories: (1) approaches involving treatment outside the vessel; (2) approaches involving treatment inside the aneurysm; and (3) approaches involving treatment in the parent vessel. Some of these approaches can be used together. Each of these approaches has some disadvantages, as discussed below.

1. Treatment Outside the Vessel

Clipping: Clipping is the application of a small clip to the aneurysm neck from outside the vessel to seal off the aneurysm. For most brain aneurysms, this involves invasive surgery including removing a section of the skull. Clipping began in the 1930's and is well-established. Clipping is more common in the U.S. than in Europe. Around half of all aneurysms are treated by clipping. There are many aneurysm clips in the prior art. However, due to its invasive nature, clipping is decreasing. Potential disadvantages of clipping can include: significant health risks associated with major surgery of this type; and long recovery times, even when the surgery itself goes well.

2. Treatment Inside the Aneurysm

Metal Coils: Metal coiling is the endovascular insertion of metal coils into the aneurysm to reduce blood flow and promote embolization in the aneurysm. Historically, metal coils have been platinum. Coils are more common in Europe than in the U.S. There are many examples of metal coils. Potential disadvantages of metal coils can include: low percentage of aneurysm volume filled (low occlusion is associated with a higher risk of rupture); compaction of coils over time; risk of recanalization; potential prolapse of coils into the parent vessel; difficulty later clipping aneurysms filled with metal coils, if needed; pressure from the coils on surrounding brain tissue; inability of coils to treat all aneurysms; and expense of metal coils (especially platinum coils).

Combination Metal/Textile/Foam/Gel Coils: Coils with a combination of metal and other materials can be used to try to achieve greater occlusion volume than metal coils alone. These other materials include textile, foam, and gel elements. Textile strands can be woven into the coils to add bulk. Coils can be covered with soft foam. Gel elements can be strung together into elongated structures. Examples of related art that appear to use this approach includes the following: U.S. Pat. No. 5,382,259 (Phelps et al.), U.S. Pat. No. 5,522,822 (Phelps et al.), U.S. Pat. No. 5,690,666 (Berenstein et al.), U.S. Pat. No. 5,718,711 (Berenstein et al.), U.S. Pat. No. 5,749,894 (Engelson), U.S. Pat. No. 5,976,162 (Doan et al.), U.S. Pat. No. 6,024,754 (Engelson), U.S. Pat. No. 6,299,619 (Greene, Jr. et al.), U.S. Pat. No. 6,602,261 (Greene, Jr. et al.), U.S. Pat. No. 6,723,108 (Jones et al.), U.S. Pat. No. 6,979,344 (Jones et al.), U.S. Pat. No. 7,070,609 (West), and U.S. Pat. No. 7,491,214 (Greene, Jr. et al.), and U.S. Patent Applications 20040158282 (Jones, Donald et al.), 20050267510 (Razack, Nasser), and 20060058834 (Do, Hiep et al.). Potential disadvantages of combination coils can include: remaining gaps between loops; compaction of coils over time; risk of recanalization; potential prolapse of coils into the parent vessel; difficulty clipping aneurysms filled with coils with metal components later if needed; pressure from the coils on surrounding brain tissue; inability of coils to treat all aneurysms; and expense of metal coils.

Inflatable Balloons: Approximately two decades ago, there were numerous efforts to treat aneurysms by permanently filling them with inflatable balloons. These efforts were largely abandoned due to the risks of balloon deflation, prolapse into the parent vessel, aneurysm rupture, and recanalization. There are, however, examples of relatively recent art that appear to use inflatable balloons to treat aneurysms: U.S. Pat. No. 6,569,190 (Whalen et al.) and U.S. Pat. No. 7,083,643 (Whalen et al.), and U.S. Patent Applications 20030135264 (Whalen et al.), 20030187473 (Berenstein, Alejandro et al.), 20060292206 (Kim, Steven et al.), 20070050008 (Kim, Steven et al.), and 20070055355 (Kim, Steven et al.). Potential disadvantages of using inflatable balloons to permanently fill aneurysms can include: balloon deflation; prolapse of the balloon into the parent vessel; aneurysm rupture due to balloon pressure; and recanalization.

Manually-Activated Mesh Occluders: Another approach to treating aneurysms involves inserting into the aneurysm a mesh structure, generally metal, that can be expanded or contracted by human-controlled mechanical motion so as to block the aneurysm neck and/or to fill the main volume of the aneurysm. For example, a wire structure can be inserted through the aneurysm neck in a narrow configuration and then transformed into an "hour-glass" shape that collapses to block the aneurysm neck when activated by a human controller. Examples of related art that appear to use this approach include the following: U.S. Pat. No. 5,928,260 (Chin et al.), U.S. Pat. No. 6,344,048 (Chin et al.), U.S. Pat. No. 6,375,668 (Gifford et al.), U.S. Pat. No. 6,454,780 (Wallace), U.S. Pat. No. 6,746,468 (Sepetka et al.), U.S. Pat. No. 6,780,196 (Chin et al.), and U.S. Pat. No. 7,229,461 (Chin et al.), and U.S. Patent Applications 20020042628 (Chin, Yem et al.), 20020169473 (Sepetka, Ivan et al.), 20030083676 (Wallace, Michael), 20030181927 (Wallace, Michael), 20040181253

(Sepetka, Ivan et al.), 20050021077 (Chin et al.), 20060155323 (Porter, Stephen et al.), 20070088387 (Eskridge, Joseph et al.), 20070106311 (Wallace, Michael et al.), and 20080147100 (Wallace, Michael). Potential disadvantages of such manually-activated metal occluders include: difficulty engaging the necks of wide-neck aneurysms; difficulty filling irregularly-shaped aneurysms with standard-shaped mesh structures; risk of rupture when pinching the aneurysm neck or pushing on the aneurysm walls; and protrusion of the proximal portion of "hour-glass" designs into the parent vessel.

Self-Expanding Standard-Shape Occluders: Another approach to treating aneurysms uses standard-shaped structures that self-expand when released into the aneurysm. For example, the structure may be a mesh of "shape memory" metal that automatically expands to a standard shape when released from the confines of the catheter walls. As another example, the structure may be a gel that expands to a standard shape when exposed to moisture. Examples of related art that appear to use this approach include the following: U.S. Pat. No. 5,766,219 (Horton), U.S. Pat. No. 5,916,235 (Guglielmi), 5,941,249 (Maynard), U.S. Pat. No. 6,409,749 (Maynard), U.S. Pat. No. 6,506,204 (Mazzocchi), U.S. Pat. No. 6,605,111 (Bose et al.), U.S. Pat. No. 6,613,074 (Mitelberg et al.), U.S. Pat. No. 6,802,851 (Jones et al.), U.S. Pat. No. 6,811,560 (Jones et al.), U.S. Pat. No. 6,855,153 (Saadat), U.S. Pat. No. 7,083,632 (Avellanet et al.), U.S. Pat. No. 7,306,622 (Jones et al.), and U.S. Pat. No. 7,491,214 (Greene, Jr. et al.), and U.S. Patent Applications 20030093097 (Avellanet, Ernesto et al.), 20030195553 (Wallace, Michael et al.), 20050033349 (Jones, Donald et al.), 20060052816 (Bates, Brian et al.), and 20060235464 (Avellanet, Ernesto et al.) and WIPO Patents WO/2006/084077 (Porter, Stephen et al.) and WO/1996/018343 (McGurk et. al.). Potential disadvantages of such self-expanding standard-shape structures can include: risk of prolapse into the parent vessel, especially for wide-neck aneurysms; difficulty occluding irregularly-shaped aneurysms with standard shape structures and associated risk of recanalization; and difficulty generating the proper amount of force (not too much or too little) when engaging the aneurysm walls with a standard-shaped self-expanding structure.

Self-Expanding Custom-Modeled Occluders: A variation on self-expanding standard-shape occluders (discussed above) are self-expanding occluders that are custom modeled before insertion so as to fit the shape of a particular aneurysm. As an example sequence—the aneurysm can be imaged, the image is used to custom model the occluding structure, the occluding structure is compressed into a catheter, the occluding structure is inserted into the aneurysm, and the occluding structure then self-expands to fill the aneurysm. The occluding structure may be made from a gel that expands upon contact with moisture. Examples of related art that appear to use this approach include the following: U.S. Pat. No. 5,766,219 (Horton), U.S. Pat. No. 6,165,193 (Greene, Jr. et al.), U.S. Pat. No. 6,500,190 (Greene, Jr. et al.), U.S. Pat. No. 7,029,487 (Greene, Jr. et al.), and U.S. Pat. No. 7,201,762 (Greene, Jr. et al.), and U.S. Patent Application 20060276831 (Porter, Stephen et al.). Potential disadvantages of self-expanding custom-modeled occluders can include: the complexity and expense of imaging and modeling irregularly-shaped aneurysms; difficulty compressing larger-size structures into a catheter; difficulty inserting the occluding structure in precisely the correct position; and difficulty getting a gelatinous surface to anchor solidly to aneurysm walls.

Congealing Liquid or Gel: Another approach to treating aneurysms involves filling an aneurysm with a liquid or gel that congeals rapidly. Examples of related art that appear to use this approach include the following: U.S. Pat. No. 6,569,190 (Whalen et al.), U.S. Pat. No. 6,626,928 (Raymond et al.), U.S. Pat. No. 6,958,061 (Truckai et al.), and U.S. Pat. No. 7,083,643 (Whalen et al.), and U.S. Patent Application 20030135264 (Whalen et al.). Potential disadvantages of a congealing liquid or gel can include: leakage of the congealing substance into the parent vessel, potentially causing a stroke; difficulty filling the entire aneurysm if the substance begins to congeal before the aneurysm is full; and seepage of toxic substances into the blood stream.

Biological or Pharmaceutical Agents: Biological and/or pharmaceutical agents can enhance the performance of a variety of mechanical treatment methods for aneurysms. For example, they can speed up the natural embolization process to occlude the aneurysm. Examples of related art that appear to use this approach include the following: U.S. Patent Applications 20060206139 (Tekulve, Kurt J.), 20070168011 (LaDuca, Robert et al.), and 20080033341 (Grad, Ygael). Currently, biological and/or pharmaceutical approaches are not sufficient as stand alone treatment approaches for many cases. Accordingly, they share most of the potential disadvantages of the baseline approach to which the biological or pharmaceutical agents are added.

Embolic-Emitting Expanding Members: Another approach involves an expanding member within the aneurysm that emits embolic elements into the aneurysm. Examples of such expanding members include bags, meshes, and nets. Examples of embolic elements include coils and congealing liquids. This can be viewed as another way to block the aneurysm neck while delivering embolics into the volume of the aneurysm. For example, the distal portion of an expanding bag may leak embolic elements into the aneurysm, but the proximal portion of the expanding member does not leak embolics into the parent vessel. Examples of related art that appear to use this approach include the following: U.S. Pat. No. 6,547,804 (Porter et al.) and U.S. Patent Applications 20040098027 (Teoh, Clifford et al.), 20060079923 (Chhabra, Manik et al.), and 20080033480 (Hardert, Michael). Potential disadvantages are as follows. Since the expanding member "leaks," it may have insufficient expansion force to adequately anchor against the aneurysm walls or to seal off the aneurysm neck. As a result of poor anchoring, the bag may prolapse into the parent vessel. Also, as a result of poor sealing of the aneurysm neck, embolics may leak into the parent vessel.

Shape Memory Structures inside Expanding Members: A variation on the shape memory approach above involves the addition of an expanding member around the shape memory structure. Examples of related art that appear to use this approach include the following: U.S. Pat. No. 5,861,003 (Latson et al.), U.S. Pat. No. 6,346,117 (Greenhalgh), U.S. Pat. No. 6,350,270 (Roue), U.S. Pat. No. 6,391,037 (Greenhalgh), and U.S. Pat. No. 6,855,153 (Saadat). The potential disadvantages of this approach are similar to those for uncovered shape memory occluders: risk of prolapse into the parent vessel, especially for wide-neck aneurysms; difficulty occluding irregularly-shaped aneurysms with standard shape structures and associated risk of recanalization; and difficulty generating the proper amount of force (not too much or too little) when engaging the aneurysm walls with a standard-shaped self-expanding structure.

Accumulating Coils inside Expanding Members: A variation on the standard coiling approach above involves the addition of an expanding member around the accumulating coils. Examples of related art that appear to use this approach include the following: U.S. Pat. No. 5,334,210 (Gianturco), U.S. Pat. No. 6,585,748 (Jeffree), and U.S. Pat. No. 7,153,323

(Teoh et al.), and U.S. Patent Applications 20060116709 (Sepetka, Ivan et al.), 20060116712 (Sepetka, Ivan et al.), and 20060116713 (Sepetka, Ivan et al.). Potential disadvantages of this approach are similar to those for coils alone, including: compaction of coils over time; risk of recanalization due to "bumpy" coil-filled expanding member; difficulty clipping aneurysms filled with metal coils later if needed; pressure from the coils on surrounding brain tissue; inability to treat all aneurysms; and expense of metal coils (especially platinum coils).

3. Treatment in the Parent Vessel

Standard (High-Porosity) Stent: A stent is a structure that is inserted into a vessel in a collapsed form and then expanded into contact with the vessel walls. Standard stents are generally highly porous, metal, and cylindrical. A high-porosity stent allows blood to flow through the stent walls if there are any branching or secondary vessels in the vessel walls. Blood flow through a stent wall into a branching or secondary vessel is desirable, but blood flow through a stent wall into an aneurysm is not. Accordingly, a high-porosity stent in the parent vessel is not a good stand-alone aneurysm treatment. A high-porosity stent in the parent vessel can, however, help to keep coils or other embolic members from escaping out of the aneurysm into the parent vessel.

Examples of related art that appear to use this approach include the following: U.S. Pat. No. 6,096,034 (Kupiecki et al., 2000), U.S. Pat. No. 6,344,041 (Kupiecki et al., 2002), U.S. Pat. No. 6,168,592 (Kupiecki et al., 2001), and U.S. Pat. No. 7,211,109 (Thompson, 2007). Potential disadvantages of this approach can include many of the problems associated with use of the embolic members alone. For example, using a high-porosity stent in the parent vessel in combination with coils in the aneurysm still leaves the following disadvantages of using coils alone: low percentage of aneurysm volume filled (and low occlusion is associated with a higher risk of rupture); compaction of coils over time; significant risk of recanalization; difficulty clipping aneurysms filled with metal coils later if needed; pressure from the coils on surrounding brain tissue; inability of coils to treat all aneurysms; and expense of metal coils (especially platinum coils).

Uniformly Low-Porosity Stent: Another approach involves inserting a uniformly low-porosity stent into the parent vessel. The low-porosity stent blocks the flow of blood through the stent walls into the aneurysm, causing beneficial embolization of the aneurysm. For example, the stent may have one or more layers that are impermeable to the flow of liquid. Unlike a standard (high-porosity) stent, this approach can be used as a stand-alone aneurysm treatment. Examples of related art that appear to use this approach include the following: U.S. Pat. No. 5,645,559 (Hachtman et al., 1997), U.S. Pat. No. 5,723,004 (Dereume et al., 1998), U.S. Pat. No. 5,948,018 (Dereume et al., 1999), U.S. Pat. No. 6,165,212 (Dereume et al., 2000), U.S. Pat. No. 6,063,111 (Hieshima et al., 2000), U.S. Pat. No. 6,270,523 (Herweck et al., 2001), U.S. Pat. No. 6,331,191 (Chobotov, 2001), U.S. Pat. No. 6,342,068 (Thompson, 2002), U.S. Pat. No. 6,428,558 (Jones et al., 2002), U.S. Pat. No. 6,656,214 (Fogarty et al., 2003), U.S. Pat. No. 6,673,103 (Golds et al., 2004), U.S. Pat. No. 6,790,225 (Shannon et al., 2004), and U.S. Pat. No. 6,786,920 (Shannon et al., 2004), and U.S. Patent Application 20080319521 (Norris et al., 2008). Potential disadvantages of this approach can include: undesirably blocking blood flow to branching or secondary vessels that are close to the aneurysm and are covered by the stent wall; difficulty achieving a snug fit across the neck of the aneurysm if the parent vessel is curved, twisted, or forked; and poor attachment of the stent with the parent vessel wall due to the impermeable nature of the stent wall.

Uniformly Intermediate-Porosity Metal Stent: This approach pursues creation of a stent with a uniform intermediate porosity that provides a compromise between the benefits of a high-porosity stent in the parent vessel (good blood flow to nearby branching or secondary vessels) and the benefits of a low-porosity stents in the parent vessel (blocking blood flow to the aneurysm). Examples of related art that appear to use this approach include the following: U.S. Pat. No. 6,770,087 (Layne et al., 2004), U.S. Pat. No. 7,052,513 (Thompson, 2006), and U.S. Pat. No. 7,306,624 (Yodfat et al., 2007), and U.S. Patent Applications 20070207186 (Scanlon et al., 2007), 20070219619 (Dieck et al., 2007), 20070276470 (Tenne, 2007), 20070276469 (Tenne, 2007), and 20080039933 (Yodfat et al., 2008). The main potential disadvantage of this approach is that it may perform neither function very well. It may unreasonably block flow to a branching or secondary vessels (causing a stroke) and may inadequately block blood flow to the aneurysm (leaving it vulnerable to rupture).

Pre-Formed Differential Porosity Stent: This approach involves creating a stent with different levels of porosity for different wall areas, before the stent is inserted into the parent vessel. The goal is two-fold: (1) to place wall areas with high porosity over openings to branching or secondary vessels; and (2) to place wall areas with low porosity over the neck of the aneurysm. Examples of related art that appear to use this approach include the following: U.S. Pat. No. 5,769,884 (Solovay, 1998), U.S. Pat. No. 5,951,599 (McCrory, 1999), U.S. Pat. No. 6,309,367 (Boock, 2001), U.S. Pat. No. 6,309,413 (Dereume et al., 2001), U.S. Pat. No. 6,165,212 (Dereume et al., 2000), U.S. Pat. No. 5,948,018 (Dereume et al.,1999), U.S. Pat. No. 5,723,004 (Dereume et al., 1998), and U.S. Pat. No. 7,186,263 (Golds et al., 2007), and U.S. Patent Applications 20070219610 (Israel, 2007), 20070239261 (Bose, et al., 2007), and 20080004653 (Sherman et al., 2008). Potential disadvantages of this approach include: difficultly matching a specific anatomic configuration (curvature, branching, neck size, etc) with a preformed stent; difficulty of precise placement of the stent to properly align the porous and non-porous areas with branching vessels and the aneurysm, respectively; and difficulty creating low porosity areas in a compressed state that maintain this low porosity in an expanded state.

Post-Implantation Filling Between Stent Wall and Vessel Wall: This approach fills the gap between the wall of the stent and the wall of the parent vessel with an embolizing substance such as a liquid or gel that solidifies after insertion. Examples of related art that appear to use this approach include the following: U.S. Pat. No. 5,769,882 (Fogarty et al., 1998) and U.S. Patent Application 20070150041 (Evans et al., 2007). Potential disadvantages of this approach include: difficulty injecting the embolizing substance through the stent wall without having it leak back into the parent vessel; leakage of embolizing liquid or gel between the stent and the parent vessel into the blood stream, where it blocks a downstream vessel and causes a stroke; challenges containing the embolic material within curving vessels or vessels with irregular walls; and difficulty using this method to fill narrow-neck aneurysms.

Post-Implantation Surface Modification: This approach creates different degrees of porosity in different wall areas after the stent is implanted. The goal is to decrease the porosity of the stent wall in the area of the aneurysm neck, but to leave the rest of the stent wall relatively porous to allow blood flow to branching or secondary members. Also, high porosity in other areas of the stent wall aids in the attachment and integration of the stent to the parent vessel. Unlike the preceding approach, this approach does not fill the gap between the stent wall and the parent vessel wall with some type of solidifying liquid, but rather modifies the wall of the stent itself This reduces the risk of embolic liquid or members leaking out between the stent and the parent vessel wall into the blood stream.

This approach remains relatively uncommon The few examples in the related art appear to expose one area of the stent wall to surface-modifying chemicals or energy emissions in order to decrease porosity of the stent wall in that area alone. Examples of related art that appear to use this approach include the following: U.S. Pat. No. 5,951,599 (McCrory, 1999) and U.S. Pat. No.7,156,871 (Jones et al., 2007). Potential disadvantages of this approach include: negative effects of surface-modifying chemicals seeping into the blood stream; negative effects of energy emissions on surrounding vessel or brain tissue; and difficulty adding enough matter to the stent wall covering the aneurysm neck by chemical or energy modification means, after stent implantation, to adequately reduce blood flow through the aneurysm neck.

To conclude this section, although there has been significant progress in developing options for treating brain aneurysms, there are still high rates of death and disability and still disadvantages to the treatment options available.

SUMMARY OF THIS INVENTION

This invention can be embodied in a stent system that is inserted into the parent vessel of an aneurysm in order to reduce blood flow to the aneurysm and promote embolization of the aneurysm. The stent wall includes an inner structure, such as an expandable metal mesh, that can be expanded from a compressed state to a resilient expanded state and an outer flexible layer, such as a flexible fabric net, that covers all or part of the inner structure. Embolic members are placed and retained in the gap between the inner structure and the outer layer in the area of the aneurysm neck in order to reduce blood flow to the aneurysm.

This invention can also be embodied in a stent to reduce blood flow to an aneurysm comprising: (a) an inner member, wherein this inner member is expanded from a first configuration to a second configuration within the parent vessel of an aneurysm, wherein the circumference of the second configuration is larger than the circumference of the first configuration; and (b) an outer member, wherein this outer member is less porous than the inner member, wherein this outer member covers or surrounds a first percentage of the surface area of the inner member when the inner structure is in the first configuration, wherein this outer member covers or surrounds a second percentage of the surface area of the inner member when the inner structure is in the second configuration, and wherein the second percentage less than the first percentage.

INTRODUCTION TO THE FIGURES

FIG. 1 shows an opaque side view of one embodiment of this stent after it has been inserted and expanded within the parent blood vessel of an aneurysm.

FIG. 2 shows an alternative view of this same embodiment, with the two layers of the stent being transparent in order to allow a clearer view of the guidewires.

FIG. 3 shows an opaque side view of this same embodiment, except that a catheter to deliver embolic members has now been slid along the guidewires to reach an opening in the inner mesh structure.

FIG. 4 shows an alternative view of this same embodiment with the two layers of the stent being transparent in order to allow a clearer view of the catheter and the embolic members.

FIG. 5 shows an opaque side view of this same embodiment, except that a plurality of embolic members have now been inserted into the gap between the inner mesh structure and the outer flexible layer in the area of the aneurysm neck.

FIG. 6 shows an alternative view of this same embodiment with the two layers of the stent being transparent in order to allow a clearer view of the catheter and the embolic members.

FIGS. 7 and 8 show this same embodiment after the detachment and withdrawal of the guidewires and catheter.

FIG. 9 shows a close-up view of guidewires attached to the inside surface of a hexagonal opening in the inner mesh structure.

FIG. 10 shows a close-up view of the distal end of the catheter as it slides along the guidewires toward the inner mesh structure.

FIG. 11 shows a close-up view of the distal end of the catheter after it has completely slid along the guidewires to reach the inner mesh structure and be aligned with an opening in this inner mesh structure.

FIG. 12 shows a close-up view of embolic members being propelled through the catheter by a flow of sterile saline solution.

FIG. 13 shows a close-up view of a plurality of embolic members having been inserted into the gap between the inner mesh structure and the outer flexible layer, with both guidewires and catheter having been withdrawn.

FIGS. 14 and 15 show examples of this stent with a high-flexibility area of the outer flexible layer that is identified by radioopaque lines and that is positioned to cover the aneurysm neck.

FIGS. 16 through 18 show an example of a stent with a sliding outer flexible layer that is connected to an inner structure along arcuate ribs.

FIGS. 19 through 21 show an example of a stent with a sliding outer flexible layer that is held onto an inner structure by arcuate ribs.

FIGS. 22 through 24 show an example of a stent with a sliding outer flexible layer that is connected to an inner structure by partially-detachable connections.

DETAILED DESCRIPTION OF THE FIGURES

FIGS. 1 through 24 show possible embodiments of this stent. However, these embodiments are not exhaustive. These figures do not limit the full generalizability of the claims.

Figure 1:
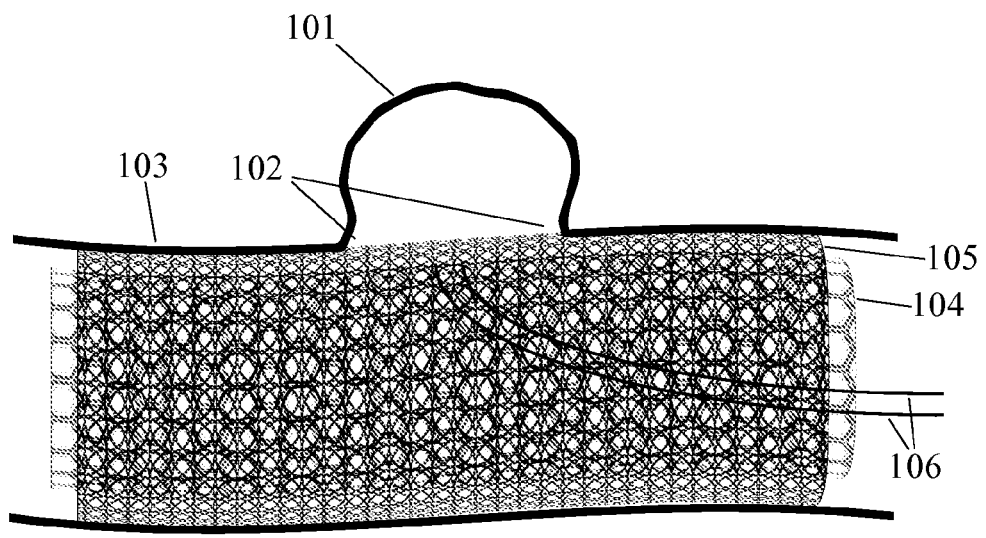
FIGS. 1 through 24 show possible embodiments of this stent, but do not limit the full generalizability of the claims.

FIG. 1 shows an opaque side view of one embodiment of this stent, after it has been inserted and expanded within the parent blood vessel of an aneurysm. FIG. 1 also shows a cross-sectional side view of the parent blood vessel 103 with aneurysm 101 including aneurysm neck 102. In this embodiment, the stent system has a resilient inner structure 104, which is a metal mesh with a hexagonal pattern, and an outer flexible layer 105 that is configured like a net around the inner structure. FIG. 1 also shows two guidewires 106 that are attached to inner structure 104. The stent is shown in FIG. 1 in an already inserted and expanded configuration. Many methods of stent insertion and expansion, such as by catheter and balloon, are well known in the art and the precise methods of insertion and expansion are not central to this invention.

In this embodiment, the wall of the stent consists of two layers. The inner layer of the stent wall is an expandable and resilient metal mesh structure 104 with a hexagonal pattern. Many other types of expandable mesh structures may also be used. In various examples, this inner mesh structure may be made from stainless steel, a nickel-titanium alloy, cobalt chromium or a cobalt-chromium alloy, titanium or a titanium alloy, tantalum or a tantalum allow, or polymeric-based resin or another polymer. In this embodiment, the outer layer of the stent is a flexible fabric net 105. In various examples, the outer flexible layer may be made from latex, nylon, polyester, teflon, silicone, HDPE, polycarbonate urethane, polyetherpolyamide copolymer, polyethylene terephthalate, polyolefin, polypropylene, polytetrafluorethylene, polytetrafluoroethene, polyurethane, or polyvinyl chloride.

In this embodiment, there is a gap between the inner mesh structure and the outer flexible layer and these layers are not connected to each other. In other examples of this invention, there may be no gap between these layers until embolic members are inserted between them in the area of the aneurysm neck. In other examples, the two layers may be connected at multiple points or seams in order to form separate pouches between the layers for more precise localized containment of the embolic members between the layers. In other examples, the wall may be comprised of more than two layers.

Figure 2:
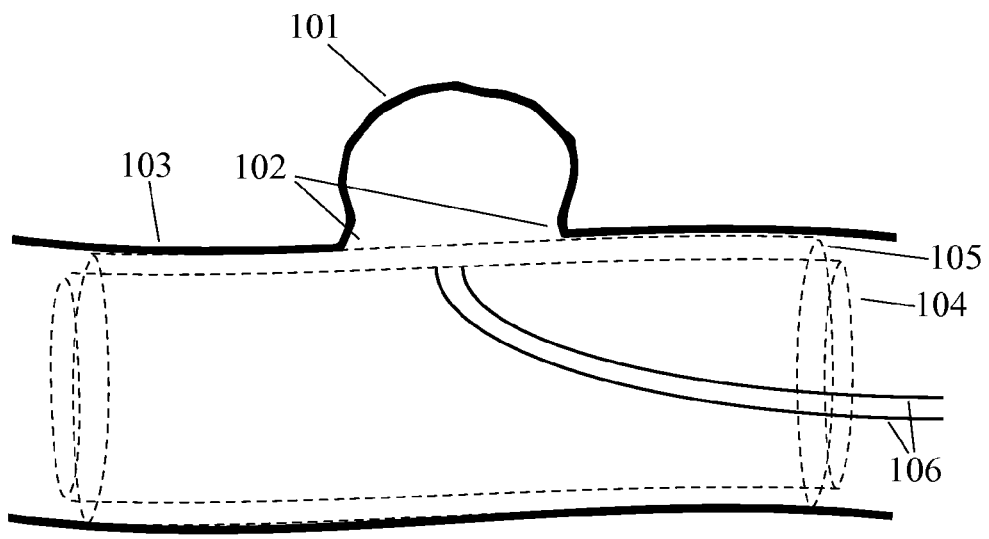

FIG. 2 shows an alternative view of the same embodiment of this stent that is shown in FIG. 1. FIG. 2 is the same as FIG. 1 except that FIG. 2 shows the two layers of the stent as transparent in order to allow a clearer view of two guidewires 106 that are attached to the inner mesh structure of the stent wall. In this embodiment, these two guidewires 106 were attached to the inner structure of the stent at a specific point before insertion of the stent and the operator has aligned this point with the aneurysm neck 102 during stent placement within the parent vessel 103. In this embodiment, these two guidewires 106 will be used to guide a catheter that delivers embolic members into the gap between the inner wall structure 104 and the outer flexible layer 105. In another example, guidewires need not be used; the catheter may be directed to the inner wall structure using real-time imaging and attached to the inner wall structure with a grasping or hooking mechanism.

Figure 3:
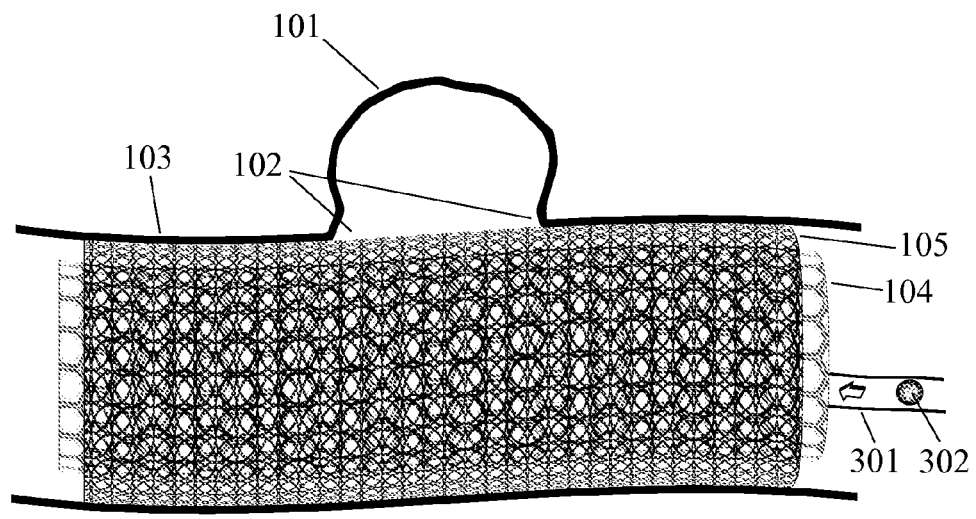

FIG. 3 shows an opaque side view of the same embodiment of this stent that is shown in FIG. 1, except that a catheter 301 to deliver embolic members (including embolic member 302) has been slid along guidewires 106 to reach an opening in the inner mesh structure 104. In this embodiment, sterile embolic members (including 302) are propelled by a flow of sterile saline solution through catheter 301 for insertion into the gap between inner mesh structure 104 and outer flexible layer 105. The saline solution propels the embolic members through the catheter and into the gap, wherein the members expand and are trapped within the gap. The saline solution escapes through the openings in the mesh. In other examples, other means may be used to transport the embolic members along the catheter, such as miniature conveyor belts or rotating helix mechanisms.

In this embodiment, the embolic members are compressible micro-sponges that expand upon ejection from the catheter. In various examples, these micro-sponges may be made from cellulose, collagen, acetate, alginic acid, carboxy methyl cellulose, chitin, collagen glycosaminoglycan, divinylbenzene, ethylene glycol, ethylene glycol dimethylmathacrylate, ethylene vinyl acetate, hyaluronic acid, hydrocarbon polymer, hydroxyethylmethacrylate, methlymethacrylate, polyacrylic acid, polyamides, polyesters, polyolefins, polysaccharides, polyurethane, polyvinyl alcohol, silicone, urethane, and vinyl stearate. In other examples, the embolic members may be gels, beads, or coils.

In this embodiment, the embolic members (such as 302) are retained with the gap between the inner mesh structure 104 and outer flexible layer 105 because they expand upon ejection from the catheter 301 and can not exit the same opening in the inner mesh structure by which they entered this gap. In another example, the embolic members need not expand, but the opening by which they enter the gap may be closed when the catheter is removed to trap them within the gap.

Figure 4:
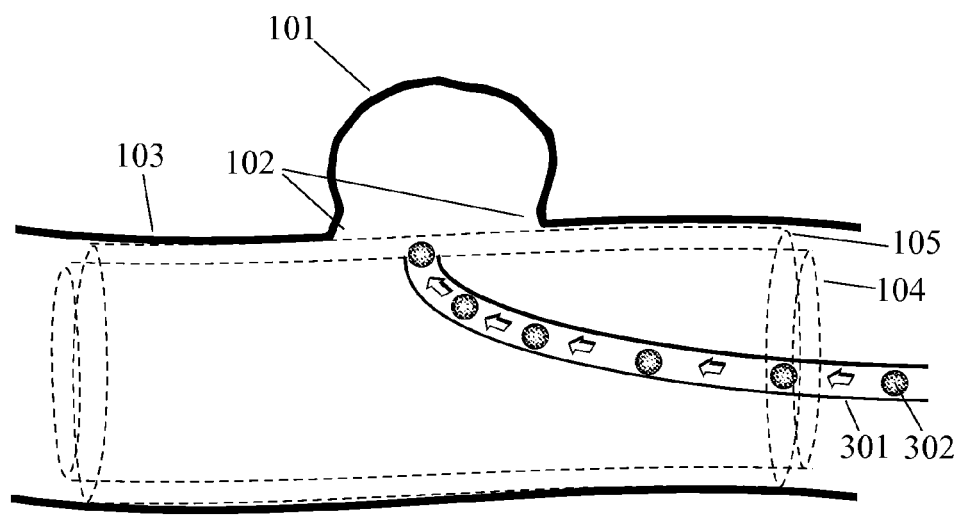

FIG. 4 shows an alternative view of the same embodiment of this stent that is shown in FIG. 3, except that the two layers of the stent are transparent in order to allow a clearer view of catheter 301 and embolic members (including 302).

Figure 5:
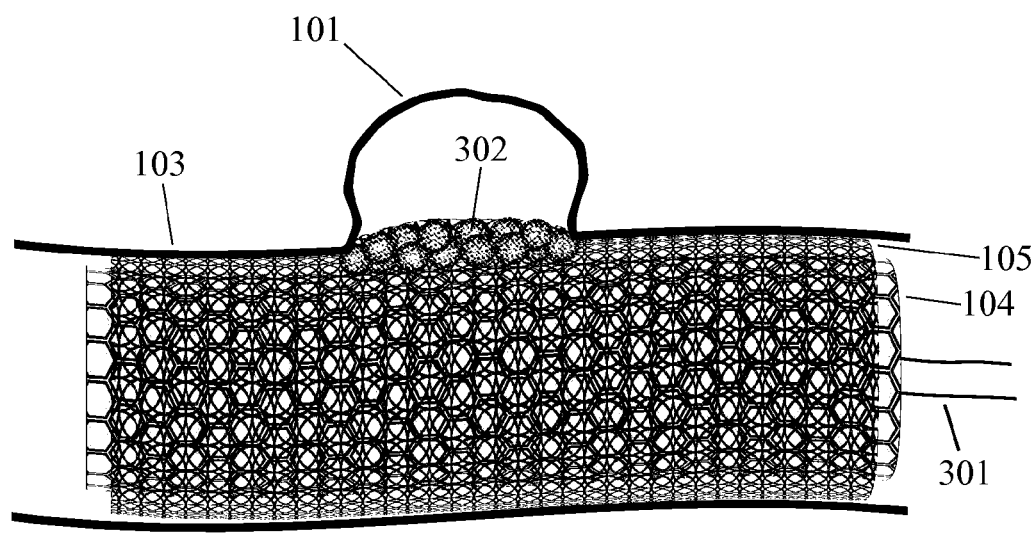

FIG. 5 shows an opaque side view of the same embodiment of this stent that is shown in FIG. 3, except that a plurality of embolic members (including 302) have now been delivered via catheter 301 and inserted into the gap between the inner mesh structure 104 and the outer flexible layer 105 in the area of the aneurysm neck. The flexibility of outer layer 105 allows it to distend into the aneurysm neck to more thoroughly block blood flow through the neck. A sufficient volume of embolic members has been inserted into this gap in the area of the aneurysm neck to occlude the flow of blood into aneurysm 101, thereby promoting embolization of the aneurysm.

Figure 6:
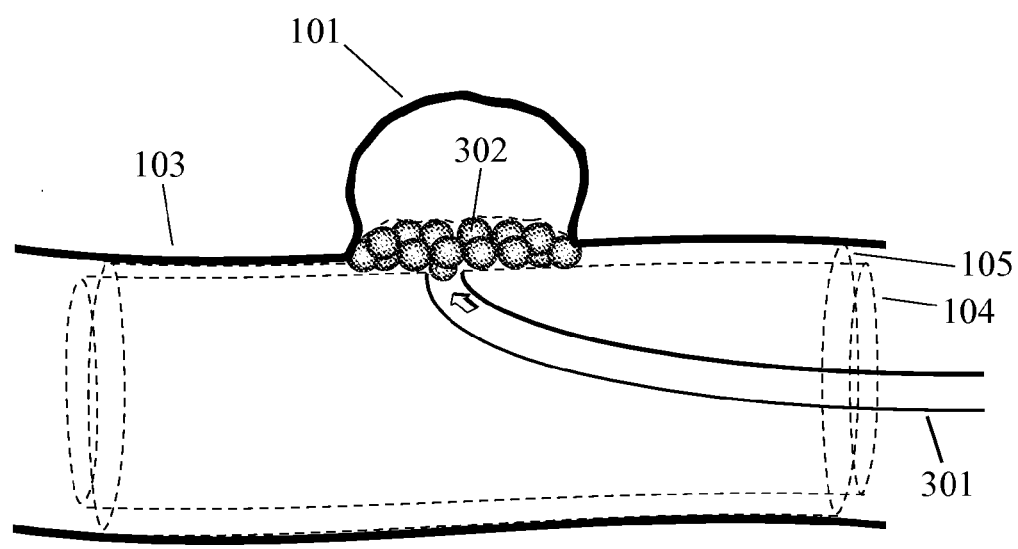

FIG. 6 shows an alternative view of the same embodiment of this stent that is shown in FIG. 5, except that the two layers of the stent are transparent in order to allow a clearer view of catheter 301 and embolic members (including 302).

Figure 7:
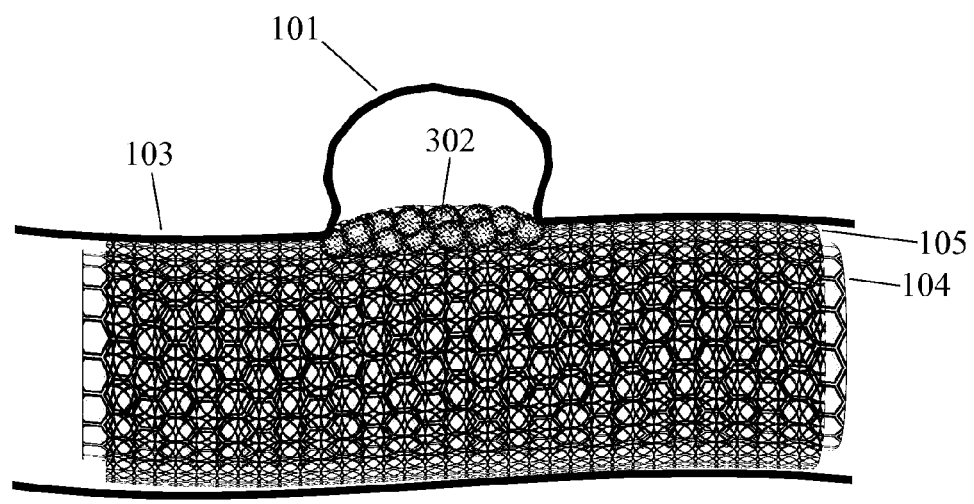
Figure 8:
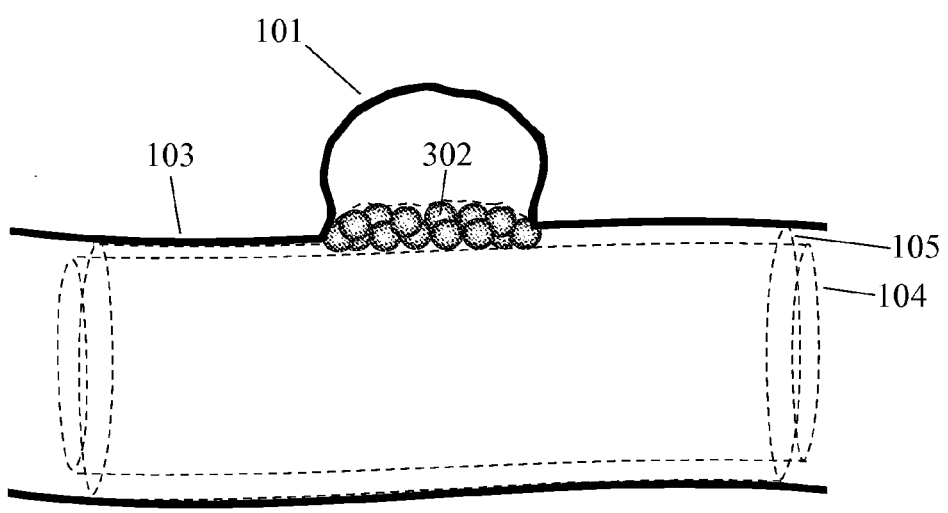

FIGS. 7 and 8 show the same embodiment, but after the detachment and withdrawal of the guidewires 106 and catheter 301. In this example, the guidewires may be detached from the inner mesh structure by application of a mild electric current and the catheter may be removed by simple mechanical withdrawal. Many other methods for detaching and removing guidewires and catheters are known in the prior art and the exact detachment and removal mechanisms are not central to this invention. Blood flow through the aneurysm neck is now largely blocked to promote embolization of the aneurysm, but other areas of the stent remain largely porous to foster integration with the walls of the parent vessel and to allow blood flow to any secondary vessels that may branch off from the parent vessel along the length of the stent.

FIGS. 9 through 13 show greater detail for one example of how the guidewires and catheter function to transport embolic members into the gap between the inner mesh structure and the outer flexible layer of the stent wall. In these figures: only small square patches of inner mesh structure 104 and outer flexible layer 105 are shown (indicated by dashed line borders); and the size of the gap between these two layers is exaggerated to provide a clearer view of how embolic members are inserted within this gap. In this example, guidewires 106 are attached to inner mesh structure 104 before the stent is inserted in the parent vessel and catheter 301 is guided to the inner mesh structure 104 by means of these guidewires.

Figure 9:
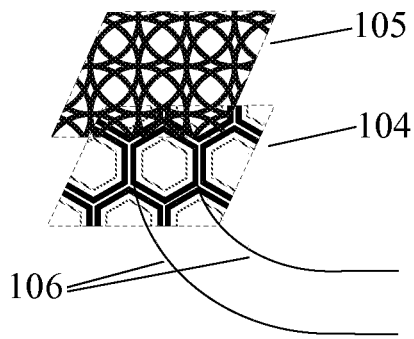
Figure 10:
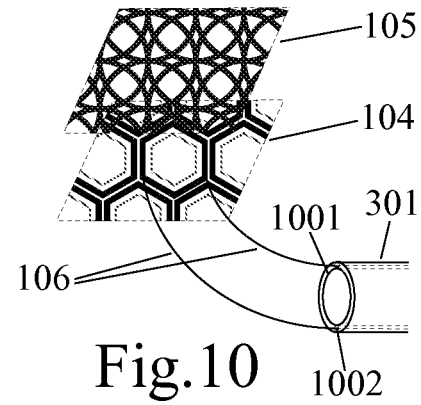
Figure 11:
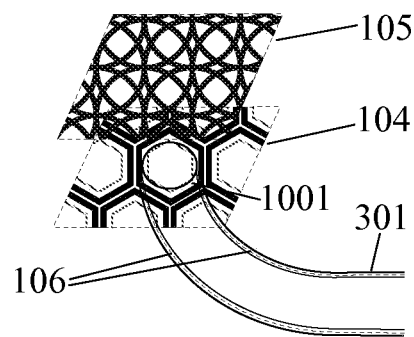

FIG. 9 shows a close-up view of guidewires 106 attached to the inside surface of a hexagonal opening in inner mesh structure 104. FIG. 9 also shows outer flexible layer 105. FIG. 9 corresponds to a close-up view of a small area of FIGS. 1 and 2, the area in which guidewires 106 are attached to inner mesh structure 104. FIG. 10 shows a close-up view of the distal end 1001 of catheter 301 as it slides along guidewires 106 toward inner mesh structure 104. The other (proximal) end of catheter 301 remains outside the person's body. There are two holes, including 1002, that run longitudinally through opposite sides of the wall of catheter 301 and contain guidewires 106, enabling catheter 301 to slide along guidewires 106. FIG. 11 shows a close-up view of the distal end 1001 of catheter 301 after it has completely slid along guidewires 106 to reach inner mesh structure 104 and be aligned with one hexagonal opening of this structure.

Figure 12:
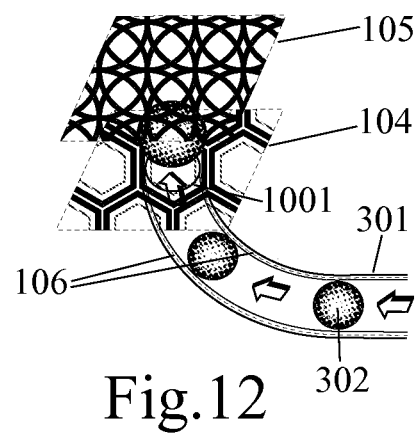

FIG. 12 shows a close-up view of embolic members (including 302) being propelled through catheter 301 by a flow of sterile saline solution. In this example, the embolic members are micro-sponges that expand upon ejection from the catheter into the gap between the inner mesh structure 104 and outer flexible layer 105. FIG. 12 corresponds to a close-up view of a small area of FIGS. 3 and 4, the area in which the guidewires 106 are attached to the inner mesh structure 104.

Figure 13:
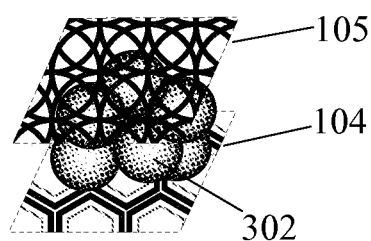

FIG. 13 shows a close-up view of a plurality of embolic members having been inserted into the gap between the inner mesh structure 104 and outer flexible layer 105. Also, guidewires 106 and catheter 301 have been detached and withdrawn. FIG. 13 corresponds to a close-up view of a small area of FIGS. 7 and 8, the area in which the guidewires were attached to the inner mesh structure.

Figure 14:
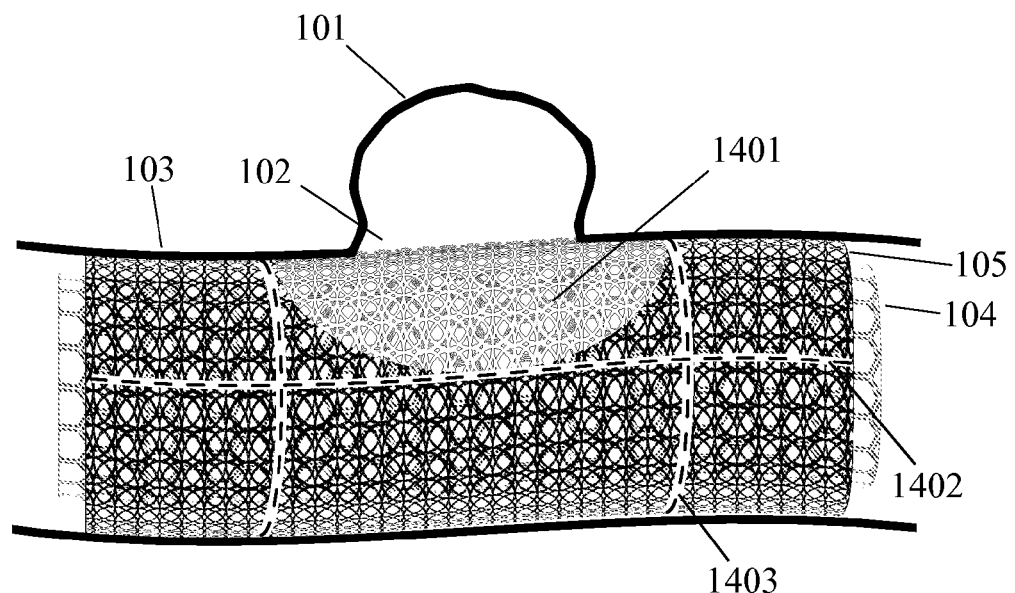
Figure 15:
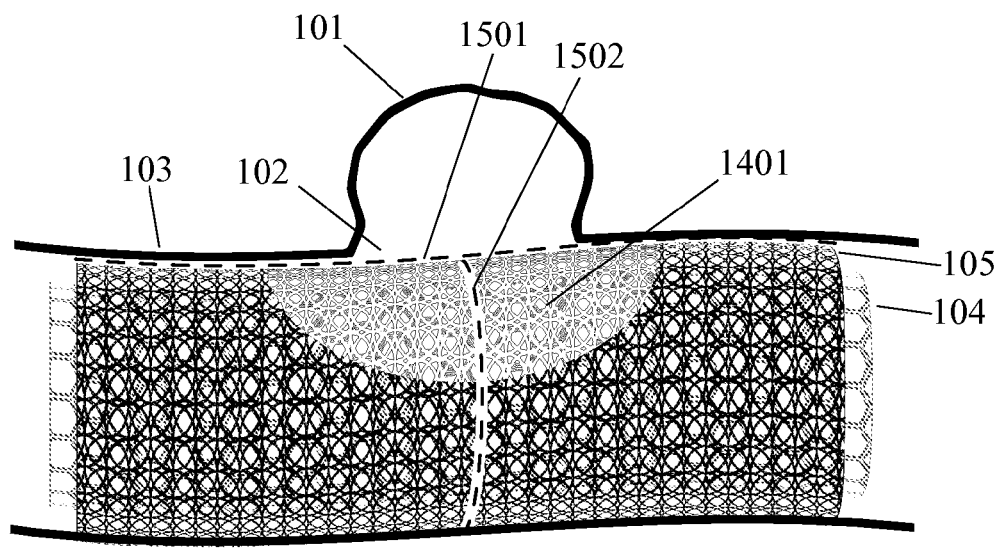

FIGS. 14 and 15 show an opaque side view of two examples of this stent that feature an outer flexible layer with differential flexibility. Having a stent with one area of the outer flexible layer that has greater flexibility and placing this area over the aneurysm neck has two advantages. First, it facilitates insertion of a substantial mass of embolic members into the gap between the inner mesh and the outer flexible layer in the area of the aneurysm neck in order to thoroughly occlude the aneurysm neck. Second, although the walls of the parent vessel resist migration of embolic members through the gap away from the aneurysm neck area, having less flexibility of the outer layer outside the aneurysm neck area provides additional resistance to possible migration of embolic members.

Specifically, FIGS. 14 and 15 show a stent, with an inner structural mesh 104 and an outer flexible net 105, having been inserted into parent vessel 103 of aneurysm 101 with aneurysm neck 102. FIGS. 14 and 15 also show a saddle-shaped area 1401 of the outer flexible net that has greater flexibility than the rest of the net. This saddle-shaped area with greater flexibility is positioned to cover the aneurysm neck when the stent is placed and expanded.

In FIGS. 14 and 15, the stent also features radioopaque lateral and longitudinal lines that help the operator to align the saddle-shaped area with the aneurysm neck during placement and expansion of the stent. In FIG. 14, the saddle-shaped area 1401 is identified for the operator by radioopaque longitudinal lines (including 1402) and lateral circumferential lines (including 1403) that intersect the outer boundaries of the saddle-shaped area. In this example, the operator positions the stent so that the aneurysm neck is centered, in each direction, between these radioopaque lines. In FIG. 15, the saddle-shaped area 1401 is identified by radioopaque longitudinal line 1501 and lateral circumferential line 1502 that intersect the center of the saddle-shaped area. In this example, the operator positions the stent so that the intersection of these lines is centered within the aneurysm neck.

In the examples shown in FIGS. 14 and 15: there is only one area of the outer flexible net with higher flexibility, this area is saddle-shaped, and this area spans approximately 15% of surface area of the stent. In other examples: there may be more than one area with higher flexibility to address multiple aneurysms, the area may have a different shape, and the area may span a higher or lower percentage of the surface area of the stent. In these examples, the radioopaque lines are lateral circumferential and longitudinal lines. In other examples, the radioopaque lines may trace the exact perimeter of the higher-flexibility area.

The following are particularly-relevant quotes from the specification thus far (including page and line numbers from the original Nov. 18, 2009 specification): "a stent system that is inserted into the parent vessel of an aneurysm in order to reduce blood flow to the aneurysm and promote embolization of the aneurysm" (Nov. 18, 2009 specification, page 10, lines 23-25); "stent wall includes an inner structure . . . that can be expanded from a compressed state to a resilient expanded state and an outer flexible layer . . . that covers . . . part of the inner structure" (Nov. 18, 2009 specification, page 10, lines 25-27); "one area of the outer flexible net . . . the area may span a higher or lower percentage of the surface area of the stent" (Nov. 18, 2009 specification, page 17, line 28-page 18, line 1); "features radioopaque lateral and longitudinal lines that help the operator to align the saddle-shaped area with the aneurysm neck during placement and expansion " (Nov. 18, 2009 specification, page 17, lines 17-19); "layers may be connected at multiple points or seams" (Nov. 18, 2009 specification, page 13, lines 30-31); and "In this embodiment . . . these layers are not connected to each other" (Nov. 18, 2009 specification, page 13, lines 27-28).

In an example, an invention can be embodied in a device that is inserted into the parent vessel of an aneurysm in order to reduce blood flow to the aneurysm, comprising: an inner structure that can be expanded from a compressed state to a resilient expanded state within the parent vessel of the aneurysm; and an outer flexible layer that covers part of the inner structure, wherein this outer flexible layer spans a first percentage of the surface area of the inner structure before expansion of the inner structure, wherein this outer flexible layer spans a second percentage of the surface area of the inner structure after expansion of the inner structure, and wherein the first percentage is higher than the second percentage. In an example, the outer flexible layer can be less porous than the inner structure. In an example, this device can further comprise radioopaque markings that help the operator to align the outer flexible layer with the aneurysm neck.

In an example, this invention can be embodied in a device that is inserted into the parent vessel of an aneurysm in order to reduce blood flow to the aneurysm, comprising: an inner structure that can be expanded from a compressed state to a resilient expanded state within the parent vessel of the aneurysm; and an outer flexible layer that covers part of the inner structure, wherein the inner structure and outer flexible layer are connected to each other at multiple points or seams, and wherein one or more of these multiple points or seams are disconnected during expansion of the inner structure. In an example, the outer flexible layer can be less porous than the inner structure. In an example, this device can further comprise radioopaque markings that help the operator to align the outer flexible layer with the aneurysm neck.

FIGS. 16 through 24 show three examples of how this invention can be embodied in a device that is inserted into the parent vessel of an aneurysm in order to reduce blood flow to the aneurysm, comprising: an inner structure that can be expanded from a compressed state to a resilient expanded state within the parent vessel of the aneurysm; and an outer flexible layer that spans a first percentage of the circumference of the inner structure before expansion of the inner structure, wherein this outer flexible layer spans a second percentage of the circumference of the inner structure after expansion of the inner structure, and wherein the first percentage is higher than the second percentage.

Figure 16:
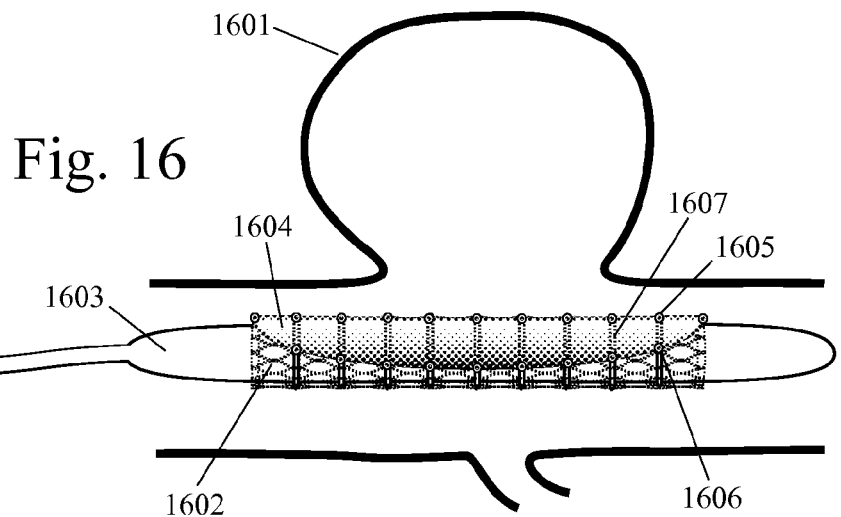
Figure 17:
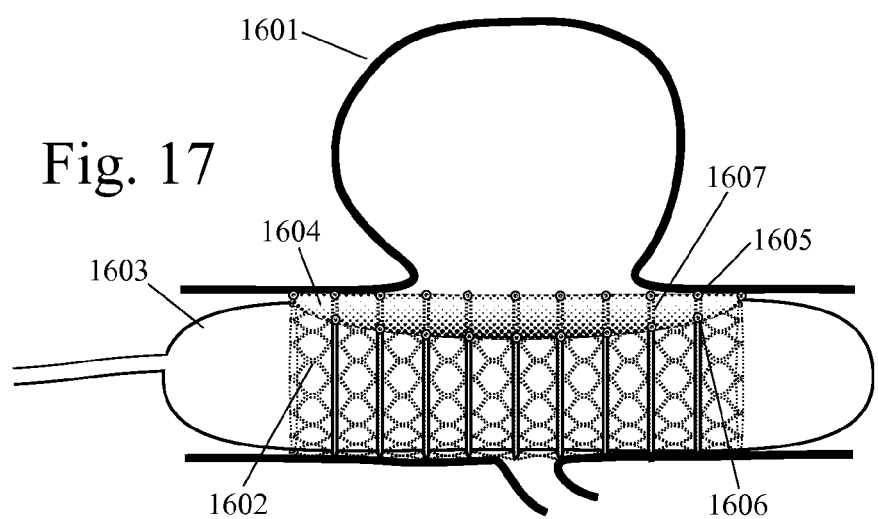
Figure 18:
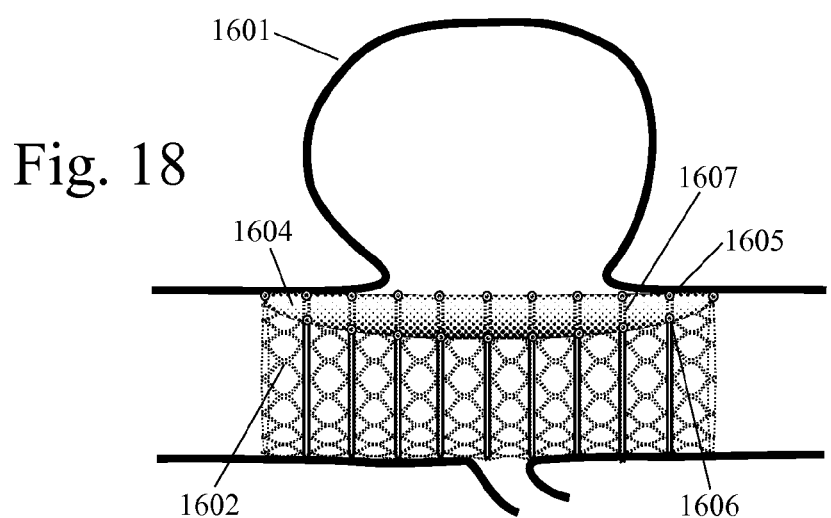

FIGS. 16 through 18 show an example of a stent with a sliding outer flexible layer that is connected to an inner structure along arcuate ribs. FIG. 16 shows a longitudinal cross-sectional view of aneurysm 1601 and a longitudinal cross-sectional view of the parent vessel of the aneurysm. FIG. 16 also shows a longitudinal side view of a device that has been inserted into the parent vessel of aneurysm 1601. FIG. 16 shows this device after the device has been placed within the parent vessel and after an outer flexible layer (1604) has been aligned with the neck of the aneurysm, but before an inner structure (1602) has been expanded. In this example, this device comprises: inner structure (1602) that can be expanded from a compressed state to a resilient expanded state; outer flexible layer (1604) that spans part of inner structure 1602; multiple points or seams (including 1605 and 1606) by which outer flexible layer 1604 is connected to inner structure 1602; multiple arcuate ribs or tracks 1607 to which the multiple points or seams (including 1605 and 1606) are attached; and inflatable member 1603 which is used to expand inner structure 1602.

In this example, inner structure 1602 is an expandable resilient tubular mesh. In this example, outer flexible layer 1604 is a saddle-shaped net, patch, covering, and/or liner with a lower porosity than inner structure 1602. In an example, outer flexible layer 1604 can have smaller surface pores or openings (as shown in FIGS. 9 through 13) and/or be less permeable to blood than inner structure 1602. In an example, outer flexible layer 1604 can be impermeable to blood. In various examples, outer flexible layer 1604 can have shapes other than a saddle shape. In an example, outer flexible layer 1604 can have a semi-tubular shape. In this example, outer flexible layer 1604 spans a first percentage of the circumference of inner structure 1602 before expansion of inner structure 1602. In this example, outer flexible layer 1604 spans (a maximum of) approximately 75% of the circumference of inner structure 1602 before expansion of inner structure 1602. In other examples, an outer flexible layer can span a pre-expansion percentage of the circumference of the inner structure in the range of 50% to 100%.

In an example, arcuate ribs or tracks (such as 1607) can encircle the entire circumference of inner structure 1602. In an example, arcuate ribs or tracks (such as 1607) can partially encircle a portion of the circumference of inner structure 1602. In an example, arcuate ribs or tracks can fully or partially encircle the circumference of inner structure 1602 in a plane which is substantially perpendicular to the longitudinal axis of inner structure 1602. In an example, arcuate ribs or tracks (such as 1607) can expand or telescope longer when inner structure 1602 expands.

In an example, inflatable member 1603 can be a balloon. In an example, inflatable member 1603 can be inflated by filling it with a liquid, such as saline or contrast media. In an example, inflatable member 1603 can be inflated by filling it with a gas, such as carbon dioxide. In an example, this device can further comprise imaging-detectable markings (as shown in FIGS. 14 and 15) to help an operator align outer flexible layer 1604 with the neck of the aneurysm. In an example, this device can further comprise radioopaque markings to help an operator align outer flexible layer 1604 with the neck of the aneurysm. In an example, this device can further comprise ultrasound-detectable markings to help an operator align outer flexible layer 1604 with the neck of the aneurysm. In an example, three-dimensional ultrasound imaging can be used to guide placement of the device and/or to align the outer layer 1604 with the neck of the aneurysm.

FIG. 16 shows this device before inner structure 1602 is expanded by expansion of inflatable member 1603. FIG. 17 shows this same device after inner structure 1602 has been expanded by expansion of inflatable member 1603. As shown in FIG. 17, the (maximum) percentage of the surface area of inner structure 1602 which is spanned by outer flexible layer 1604 is smaller after expansion of inner structure 1602. This is because outer flexible layer 1604 has been expanded less, or not at all, during the expansion of inner structure 1602. As also shown in FIG. 17, the (maximum) percentage of the circumference of inner structure 1602 which is spanned by outer flexible layer 1604 is smaller after the expansion of inner structure 1602. This is because outer flexible layer 1604 has been expanded less, or not at all, during the expansion of inner structure 1602. In this example, the post-expansion percentage of the circumference of inner structure 1602 which is spanned by outer flexible layer 1604 is approximately 30%. In an example, this percentage can be in the range of 20% to 60%

As shown in FIGS. 16 and 17, outer flexible layer 1604 spans a first (pre-expansion) percentage of the circumference of inner structure 1602 before inner structure 1602 is expanded, spans a second (post-expansion) percentage of the circumference of inner structure 1602 after inner structure is expanded, and the first percentage is larger than the second percentage. This is because the surface area of the outer flexible layer 1604 expands less (or not at all) relative to the expansion of inner structure 1602. This differential expansion of outer flexible layer 1604 vs. inner structure 1602 creates a region of low-porosity over the aneurysm neck. This advantageously helps to block blood flow through the aneurysm without deleteriously blocking blood flow to nearby branching blood vessels (such as the small branching vessel shown on side of the parent vessel which is opposite the aneurysm neck).

In the example shown in FIGS. 16 and 17, outer flexible layer 1604 has less expansion (or none at all) compared to the expansion of inner structure 1602 because outer flexible layer 1604 is connected to inner structure 1602 by means of multiple points or seams (such as 1605 and 1606) which are able to slide along multiple arcuate ribs or tracks (such as 1607) along the circumference of inner structure 1602. In this example, when inner structure 1602 is expanded, outer flexible layer 1604 does not expand. In this example, when inner structure 1602 is expanded, outer flexible layer 1604 slides on the arcuate ribs or tracks via multiple points or seams (including 1606). This is why, in this example, outer flexible layer 1604 (which does not expand) covers a smaller percentage of the surface area of inner structure 1602 (which does expand) after inner structure 1602 has been expanded.

In an example, inner structure 1602 and outer flexible layer 1604 can be connected at multiple points or seams and one or more of these points or seams can move along the circumference of the inner structure during expansion of the inner structure. In an example, inner structure 1602 and outer flexible layer 1604 can be connected at multiple points or seams and one or more of these points or seams can move on a track along the circumference of the inner structure during expansion of the inner structure.

In the example shown in FIGS. 16 and 17, a first subset (including 1606) of the multiple points or seams can slide along arcuate ribs or tracks (such as 1607) when inner structure 1602 expands, but a second subset (including 1605) of the multiple points or seams does not slide. Having a first subset (including 1606) of multiple points or seams slide allows outer flexible layer 1604 to not expand when inner structure 1602 expands. Having a second subset (including 1605) of multiple points or seams which do not slide helps to keep outer flexible layer 1604 properly positioned over the aneurysm neck during expansion of inner structure 1602. FIG. 18 shows the same device that was shown in FIGS. 16 and 17, but in a final configuration after inflatable member 1603 has been removed.

Figure 19:
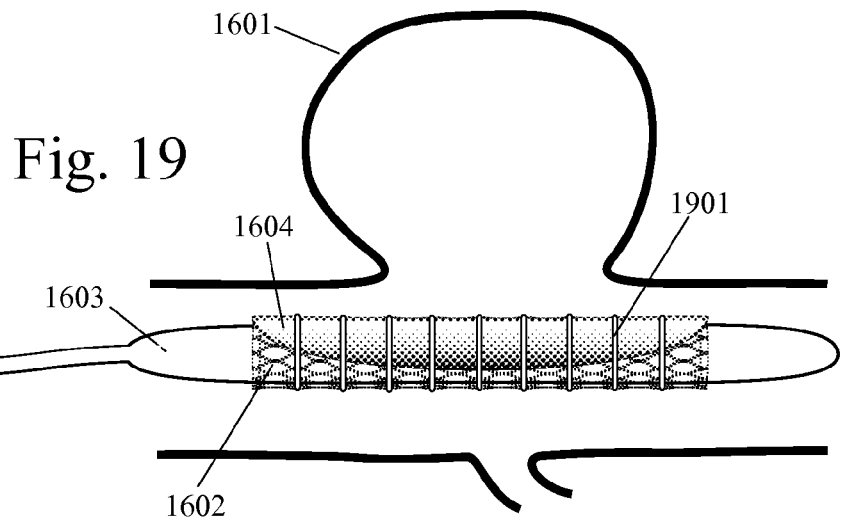
Figure 20:
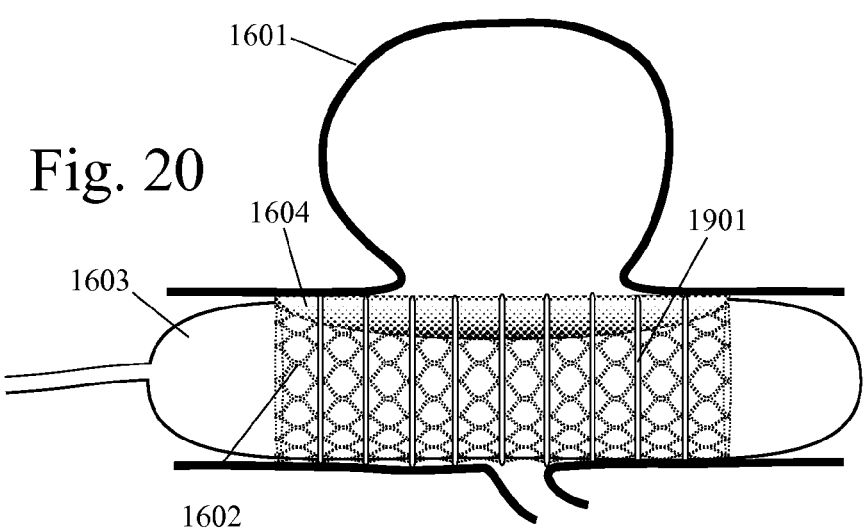
Figure 21:
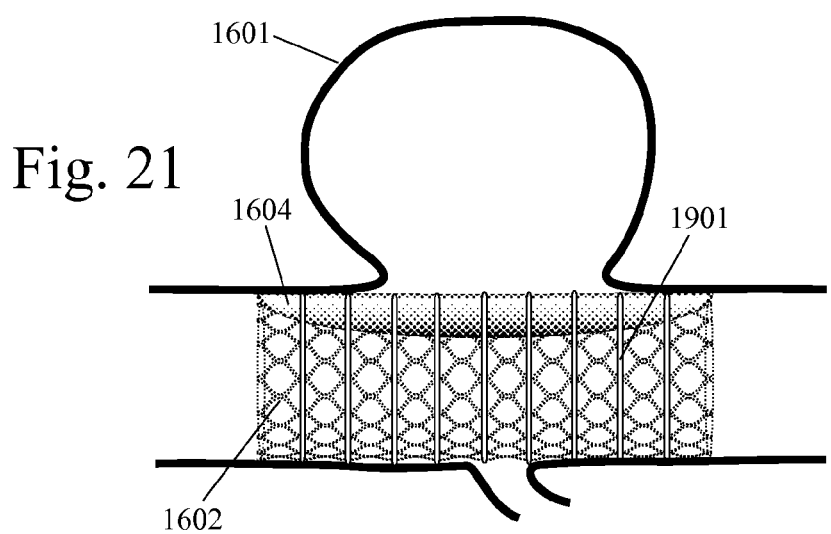

FIGS. 19 through 21 show an example of a stent with a sliding outer flexible layer that is held onto an inner structure by arcuate ribs. FIG. 19 shows this device before inner structure (1602) has been expanded. The device shown in FIG. 19 comprises: inner structure (1602) that can be expanded from a compressed state to a resilient expanded state; outer flexible layer (1604) that spans part of inner structure 1602; multiple arcuate ribs (including 1901) outside outer flexible layer 1604; and inflatable member 1603 which is used to expand inner structure 1602. Similar to the previous example, inner structure 1602 is an expandable resilient tubular mesh. Also, outer flexible layer 1604 is again a saddle-shaped net, patch, covering, and/or liner with a lower porosity than inner structure 1602. FIG. 19 shows this device before inner structure 1602 is expanded. FIG. 20 shows this device after inner structure 1602 has been expanded. FIG. 21 shows this device in a final configuration after inflatable member 1603 has been removed.

However, in this example, arcuate ribs (such as 1901) are outside outer flexible layer 1604. In this example, arcuate ribs (such as 1901) loosely hold outer flexible layer 1604 against inner structure 1602, but still allow outer flexible layer 1604 to slide around the circumference of inner structure 1602 when inner structure 1602 expands. In an example, these arcuate ribs can encircle the entire circumference of inner structure 1602. In an example, these arcuate ribs can partially encircle a portion of the circumference of inner structure 1602. In an example, these arcuate ribs can expand or telescope longer when inner structure 1602 expands. In an example, outer flexible layer 1604 is between inner structure 1602 and a plurality of expandable arcuate ribs, wherein these ribs span all or part of the circumference of inner structure, and wherein the outer flexible layer can slide between the inner structure and the expandable arcuate ribs during expansion of the inner structure. In an alternative example, the use of a flexible third layer (such as a tubular net or mesh) can serve the same function as arcuate ribs, instead of using arcuate ribs. In an example, the wall of the device may be comprised of more than two layers.

Figure 22:
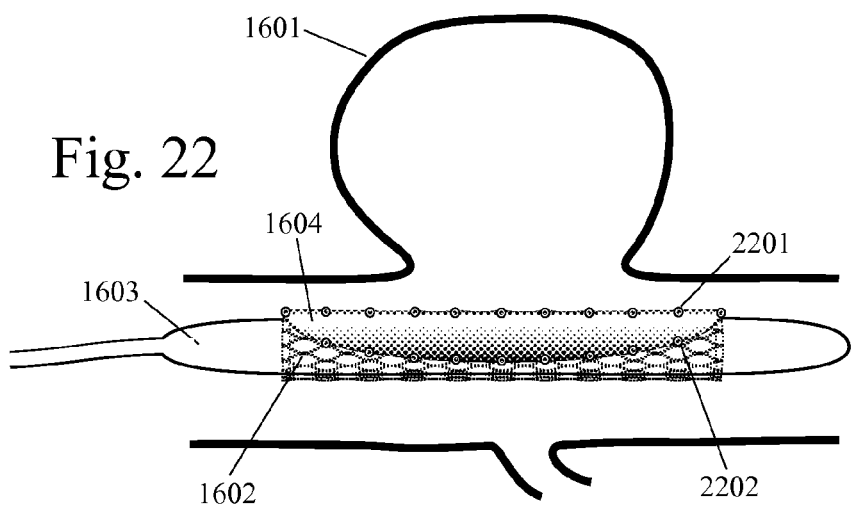
Figure 23:
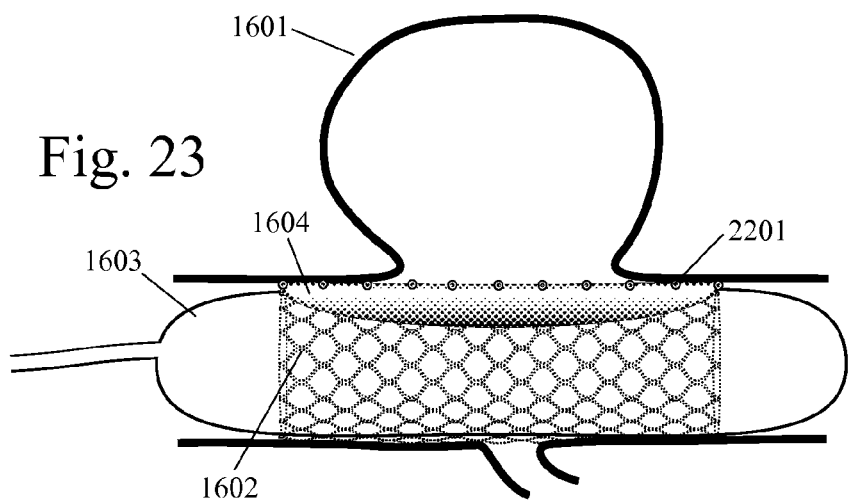
Figure 24:
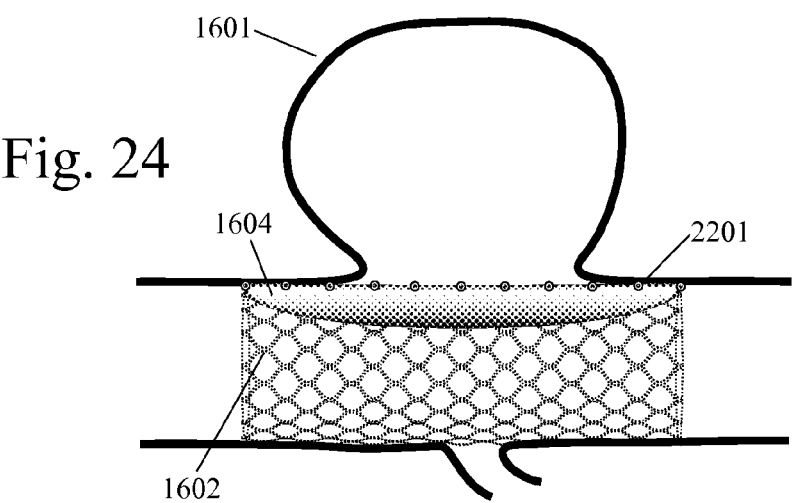

FIGS. 22 through 24 show an example of a stent with a sliding outer flexible layer that is connected to an inner structure by partially-detachable connections. FIG. 22 shows this device before an inner structure (1602) has been expanded. The device shown in FIG. 22 comprises: inner structure (1602) that can be expanded from a compressed state to a resilient expanded state; outer flexible layer (1604) that spans part of inner structure 1602; multiple points or seams (including 2201 and 2202) by which outer flexible layer 1604 is connected to inner structure 1602; and inflatable member 1603 which is used to expand inner structure 1602. Similar to the previous example, inner structure 1602 is again an expandable resilient tubular mesh and outer flexible layer 1604 is again a saddle-shaped net, patch, covering, and/or liner with a lower porosity than inner structure 1602. FIG. 22 shows this device before inner structure 1602 is expanded. FIG. 23 shows this device after inner structure 1602 has been expanded. FIG. 24 shows this device in a final configuration after inflatable member 1603 has been removed.

In this example, a subset (including 2202) of multiple points or seams (including 2201 and 2202) become disconnected when inner structure 1602 expands. This is another way to allow inner structure 1602 to expand without making outer flexible layer 1604 also expand. The subset of points or seams (including 2201) which remain connected when inner structure 1602 expands help to keep outer flexible layer 1604 positioned over the aneurysm neck. This is another way to create a low-porosity region over the aneurysm neck to block blood flow to the aneurysm without blocking blood flow to nearby branching vessels. In an example, the subset of multiple points or seams (including 2202) can become disconnected due to the shearing force of expansion. In an example, the subset of multiple points or seams (including 2202) can become disconnected via melting due to the application of an electrical charge. In an example, inner structure 1602 and outer flexible layer 1604 can be connected at multiple points or seams, wherein these one or more of these points or seams are disconnected during expansion of the inner structure.

In an example, this invention can be embodied in a stent to reduce blood flow to an aneurysm comprising: (a) an inner member, wherein this inner member is expanded from a first configuration to a second configuration within the parent vessel of an aneurysm, wherein the circumference of the second configuration is larger than the circumference of the first configuration; and (b) an outer member, wherein this outer member is less porous than the inner member, wherein this outer member covers or surrounds a first percentage of the surface area of the inner member when the inner structure is in the first configuration, wherein this outer member covers or surrounds a second percentage of the surface area of the inner member when the inner structure is in the second configuration, and wherein the second percentage is lower than the first percentage. In an example, the second percentage can be at least 10% less than the first percentage.

We claim:
1. A stent to reduce blood flow to an aneurysm comprising:
   (a) an inner member, wherein this inner member is expanded from a first configuration to a second configuration within a parent vessel of an aneurysm, wherein a circumference of the second configuration is larger than a circumference of the first configuration; and
   (b) an outer member, wherein said outer member is less porous than the inner member, wherein said outer member covers or surrounds a first percentage of a surface area of the inner member when the inner member is in the first configuration, wherein said outer member covers or surrounds a second percentage of the surface area of the inner member when the inner member is in the second configuration, wherein the second percentage is lower than the first percentage, wherein the outer member is between the inner member and a plurality of expandable arcuate ribs, wherein said plurality of expandable arcuate ribs span all or part of the circumference of inner member, and wherein the outer member can slide between the inner member and said plurality of arcuate ribs during expansion of the inner member.

* * * * *